(12) United States Patent
Hall et al.

(10) Patent No.: US 11,730,168 B2
(45) Date of Patent: Aug. 22, 2023

(54) ANTIMICROBIAL SUPERABSORBENT COMPOSITIONS

(71) Applicant: Matoke Holdings Limited, Abingdon (GB)

(72) Inventors: Thomas Hall, Birmingham (GB); Sophie Constance Cox, Birmingham (GB); Liam Michael Grover, Birmingham (GB); David Kershaw, Abingdon (GB)

(73) Assignee: Matoke Holdings Limited, Abingdon (GB)

( * ) Notice: Subject to any disclaimer, the term of this patent is extended or adjusted under 35 U.S.C. 154(b) by 0 days.

(21) Appl. No.: 16/753,570

(22) PCT Filed: Oct. 16, 2018

(86) PCT No.: PCT/GB2018/052976
§ 371 (c)(1),
(2) Date: Apr. 3, 2020

(87) PCT Pub. No.: WO2019/077335
PCT Pub. Date: Apr. 25, 2019

(65) Prior Publication Data
US 2020/0289701 A1    Sep. 17, 2020

(30) Foreign Application Priority Data
Oct. 16, 2017  (GB) ..................... 1716986

(51) Int. Cl.
| | | |
|---|---|---|
| A61K 38/44 | (2006.01) | |
| A61K 38/48 | (2006.01) | |
| A61L 26/00 | (2006.01) | |
| A01N 63/50 | (2020.01) | |
| A01N 59/00 | (2006.01) | |
| A61K 9/06 | (2006.01) | |
| A61K 38/36 | (2006.01) | |
| A61K 47/26 | (2006.01) | |
| A61K 47/32 | (2006.01) | |
| A61K 47/40 | (2006.01) | |

(52) U.S. Cl.
CPC ............ *A01N 59/00* (2013.01); *A01N 63/50* (2020.01); *A61K 9/06* (2013.01); *A61K 38/363* (2013.01); *A61K 38/443* (2013.01); *A61K 38/4833* (2013.01); *A61K 47/26* (2013.01); *A61K 47/32* (2013.01); *A61K 47/40* (2013.01); *A61L 26/008* (2013.01); *A61L 26/0014* (2013.01); *A61L 26/0042* (2013.01); *A61L 26/0047* (2013.01); *A61L 26/0066* (2013.01); *A61L 26/0095* (2013.01); *C12Y 101/03004* (2013.01)

(58) Field of Classification Search
None
See application file for complete search history.

(56) References Cited

U.S. PATENT DOCUMENTS

| | | | |
|---|---|---|---|
| 1,987,893 A | | 1/1935 | Dyce et al. |
| 2,997,397 A | * | 8/1961 | Doulgheridis ......... B65D 51/16 426/118 |
| 3,770,588 A | | 11/1973 | Forgione |
| 4,537,763 A | | 8/1985 | Miyake et al. |
| 4,537,764 A | | 8/1985 | Pellico et al. |
| 4,576,817 A | | 3/1986 | Montgomery et al. |
| 4,578,265 A | | 3/1986 | Pellico et al. |
| 4,617,190 A | | 10/1986 | Montgomery |
| 4,776,062 A | | 10/1988 | Bacon |
| 4,961,939 A | | 10/1990 | Antrim et al. |
| 5,167,950 A | | 12/1992 | Lins |
| 5,389,369 A | | 2/1995 | Allen |
| 5,451,402 A | | 9/1995 | Allen |
| 5,510,104 A | | 4/1996 | Allen |
| 5,565,197 A | | 10/1996 | Allen |
| 5,607,681 A | | 3/1997 | Galley et al. |
| 5,718,896 A | | 2/1998 | Allen |
| 5,730,933 A | | 3/1998 | Peterson |
| 5,756,090 A | | 5/1998 | Allen |
| 5,888,505 A | | 3/1999 | Allen |
| 5,980,875 A | | 11/1999 | Mousa |
| 6,033,662 A | | 3/2000 | Allen |
| 6,100,080 A | | 8/2000 | Johansen |
| 6,103,245 A | | 8/2000 | Clark et al. |
| 6,214,339 B1 | | 4/2001 | Pellico |
| 6,294,168 B1 | | 9/2001 | Allen |

(Continued)

FOREIGN PATENT DOCUMENTS

| | | |
|---|---|---|
| AU | 2003234758 | 3/2004 |
| CN | 1409636 A | 12/2000 |

(Continued)

OTHER PUBLICATIONS

Riswati et al. (Sugarcane bagasse for environmentally super absorbent polymer: synthesis methods and potential applications in oil industry, 2nd International Conference Earth Science and Energy 819 (2021) (Year: 2021).*

(Continued)

*Primary Examiner* — Melissa S Mercier

(74) *Attorney, Agent, or Firm* — Bozicevic Field & Francis, LLP; Paula A. Borden; Mandar A. Joshi

(57) ABSTRACT

A composition has an enzyme that is able to convert a substrate to release hydrogen peroxide; a substrate for the enzyme; and a superabsorbent component, such as a superabsorbent polymer. The composition is in the form of a powder and may form a gel on contact with water.

17 Claims, 16 Drawing Sheets

(56) References Cited

U.S. PATENT DOCUMENTS

| | | |
|---|---|---|
| 6,503,507 B1 | 1/2003 | Allen |
| 6,656,702 B1 | 12/2003 | Yugawa et al. |
| 6,716,611 B2 | 4/2004 | Dana et al. |
| 6,774,111 B1 | 8/2004 | Wolf et al. |
| 6,932,979 B2 | 8/2005 | Gergely et al. |
| 6,956,144 B2 | 10/2005 | Molan |
| 7,060,311 B1 | 6/2006 | Milani et al. |
| 7,399,400 B2 | 7/2008 | Soundarrajan et al. |
| 7,563,224 B2 | 7/2009 | Puchek |
| 7,714,183 B2 | 5/2010 | Caskey |
| 7,731,954 B2 | 6/2010 | Davis et al. |
| 7,927,588 B2 | 4/2011 | Davis et al. |
| 8,026,407 B2 | 9/2011 | Downs et al. |
| 8,343,552 B2 | 1/2013 | Huang et al. |
| 8,679,526 B2 | 3/2014 | Van Den Plas et al. |
| 8,679,796 B2 | 3/2014 | Reis et al. |
| 8,871,248 B2 | 10/2014 | Rodeheaver et al. |
| 8,879,575 B2 | 11/2014 | Zheng et al. |
| 8,895,282 B2 | 11/2014 | Tano |
| 8,945,540 B2 | 2/2015 | Becquerelle et al. |
| 8,986,716 B2 | 3/2015 | Gonry et al. |
| 8,999,720 B2 | 4/2015 | Kristensen et al. |
| 9,283,278 B2 | 3/2016 | Rodeheaver et al. |
| 9,333,260 B2 | 5/2016 | Pellico et al. |
| 9,393,249 B2 | 7/2016 | Barrett et al. |
| 9,421,287 B2 | 8/2016 | Kristensen et al. |
| 9,452,237 B2 | 9/2016 | Leech et al. |
| 9,522,165 B2 | 12/2016 | Barrett et al. |
| 9,661,876 B2 | 5/2017 | Mua et al. |
| 9,861,560 B2 | 1/2018 | Bernard et al. |
| 9,994,725 B2 | 6/2018 | Svoboda et al. |
| 2002/0028197 A1* | 3/2002 | Fitchett ............... A23L 29/262 424/94.4 |
| 2002/0087106 A1 | 7/2002 | Unger et al. |
| 2002/0119136 A1 | 8/2002 | Johansen |
| 2002/0150621 A1 | 10/2002 | Kohane et al. |
| 2002/0150626 A1 | 10/2002 | Kohane et al. |
| 2002/0182600 A1 | 12/2002 | Smith |
| 2003/0228264 A1 | 12/2003 | Perna |
| 2004/0054313 A1 | 3/2004 | Molan |
| 2004/0127826 A1 | 7/2004 | Caskey |
| 2004/0131693 A1 | 7/2004 | Postmes |
| 2005/0033213 A1 | 2/2005 | Bray et al. |
| 2005/0181026 A1 | 8/2005 | Davis et al. |
| 2005/0221029 A1 | 10/2005 | Cater et al. |
| 2005/0238635 A1 | 10/2005 | Tano |
| 2006/0034816 A1 | 2/2006 | Davis et al. |
| 2006/0034935 A1 | 2/2006 | Pronovost et al. |
| 2006/0099166 A1 | 5/2006 | Vandeputte |
| 2006/0142684 A1 | 6/2006 | Shanbrom |
| 2006/0165802 A1 | 7/2006 | Lotzbeyer et al. |
| 2006/0275350 A1 | 12/2006 | Davis et al. |
| 2006/0281165 A1 | 12/2006 | Davis et al. |
| 2007/0003632 A1 | 1/2007 | Lapointe et al. |
| 2007/0190122 A1 | 8/2007 | Davis et al. |
| 2007/0207215 A1 | 9/2007 | Abashidze et al. |
| 2008/0033329 A1 | 2/2008 | Downs et al. |
| 2008/0125617 A1 | 5/2008 | Puchek |
| 2008/0169217 A1 | 7/2008 | Bonneau et al. |
| 2008/0305096 A1 | 12/2008 | Verdegem et al. |
| 2008/0312572 A1 | 12/2008 | Riesinger |
| 2009/0020261 A1 | 1/2009 | McMillan et al. |
| 2009/0148537 A1 | 6/2009 | Molan et al. |
| 2009/0202615 A1 | 8/2009 | Rodeheaver et al. |
| 2009/0263467 A1 | 10/2009 | Joshi |
| 2009/0291122 A1 | 11/2009 | Vandeputte |
| 2009/0317474 A1 | 12/2009 | Van Den Plas et al. |
| 2010/0028408 A1 | 2/2010 | Vandeputte |
| 2010/0049262 A1 | 2/2010 | Puchek |
| 2010/0095645 A1 | 4/2010 | Tippery et al. |
| 2010/0098645 A1 | 4/2010 | Barrett et al. |
| 2010/0111920 A1 | 5/2010 | Pellico et al. |
| 2010/0135926 A1 | 6/2010 | Barrett |
| 2010/0143534 A1 | 6/2010 | Brinker et al. |
| 2010/0150897 A1 | 6/2010 | Pellico et al. |
| 2010/0158885 A1 | 6/2010 | Huang et al. |
| 2010/0189707 A1 | 7/2010 | Barnett |
| 2010/0233283 A1 | 9/2010 | Moloney |
| 2011/0039004 A1 | 2/2011 | Garter |
| 2011/0044966 A1 | 2/2011 | Tano |
| 2011/0052557 A1 | 3/2011 | Huang et al. |
| 2011/0052664 A1 | 3/2011 | Tennican et al. |
| 2011/0059062 A1 | 3/2011 | Pellico |
| 2011/0070198 A1 | 3/2011 | Huang et al. |
| 2011/0117071 A1 | 5/2011 | Barrett et al. |
| 2011/0135621 A1 | 6/2011 | Miller et al. |
| 2011/0159104 A1 | 6/2011 | Teslenko |
| 2011/0250256 A1 | 10/2011 | Hyun-Oh et al. |
| 2011/0263528 A1 | 10/2011 | Keiji et al. |
| 2012/0021061 A1 | 1/2012 | Schlothauer et al. |
| 2012/0058074 A1* | 3/2012 | Braig ............... A61L 15/38 424/76.6 |
| 2012/0244091 A1 | 9/2012 | Chopra et al. |
| 2012/0258087 A1 | 10/2012 | Jedlinski et al. |
| 2012/0269879 A1 | 10/2012 | Watson |
| 2013/0029030 A1 | 1/2013 | Larsen |
| 2013/0098775 A1 | 4/2013 | Pei et al. |
| 2013/0101661 A1 | 4/2013 | Rodeheaver et al. |
| 2013/0273020 A1 | 10/2013 | Gannabathula et al. |
| 2014/0023597 A1 | 1/2014 | Barrett et al. |
| 2014/0120076 A1 | 5/2014 | Stephens et al. |
| 2014/0127283 A1 | 5/2014 | Watson |
| 2014/0134213 A1 | 5/2014 | O'Flaherty et al. |
| 2014/0154193 A1 | 6/2014 | Barrett et al. |
| 2014/0199266 A1 | 7/2014 | Park et al. |
| 2014/0308399 A1 | 10/2014 | Domingues |
| 2014/0316353 A1 | 10/2014 | Riesinger |
| 2015/0009909 A1 | 1/2015 | Lundgren et al. |
| 2015/0030688 A1 | 1/2015 | Sell et al. |
| 2015/0079196 A1 | 3/2015 | Chakravarthy et al. |
| 2015/0080815 A1 | 3/2015 | Chakravarthy et al. |
| 2015/0099009 A1 | 4/2015 | Rodeheaver et al. |
| 2015/0182563 A1 | 7/2015 | Park et al. |
| 2015/0189907 A1 | 7/2015 | Donaldson et al. |
| 2015/0282513 A1 | 10/2015 | Cook et al. |
| 2015/0297644 A1 | 10/2015 | Park et al. |
| 2015/0366245 A1 | 12/2015 | Van Egeren et al. |
| 2016/0101210 A1 | 4/2016 | Watson |
| 2016/0144004 A1 | 5/2016 | Pellico |
| 2016/0151533 A1 | 6/2016 | Rodeheaver et al. |
| 2016/0186230 A1 | 6/2016 | Kaneda |
| 2016/0199421 A1 | 7/2016 | Kuehne et al. |
| 2016/0220722 A1 | 8/2016 | Wardell |
| 2016/0279205 A1 | 9/2016 | Pellico et al. |
| 2017/0049111 A1 | 2/2017 | Patton et al. |
| 2017/0072024 A1 | 3/2017 | Malepeyre et al. |
| 2017/0166938 A1 | 6/2017 | Nagy et al. |
| 2017/0202869 A1 | 7/2017 | Madsen, II et al. |
| 2017/0266240 A1 | 9/2017 | Patton et al. |
| 2017/0304452 A1 | 10/2017 | Asaruddin |
| 2018/0133358 A1 | 5/2018 | Cullen et al. |
| 2018/0177723 A1 | 6/2018 | Devraj |
| 2019/0167482 A1* | 6/2019 | Kawaguchi ........ D04H 1/43832 |
| 2020/0289701 A1 | 9/2020 | Hall et al. |

FOREIGN PATENT DOCUMENTS

| | | |
|---|---|---|
| CN | 101909666 A | 12/2010 |
| CN | 106470548 A | 3/2017 |
| DE | 4238779 A1 | 5/1994 |
| DE | 10359316 | 7/2005 |
| DE | 102012100842 | 2/2012 |
| EP | 0149096 | 7/1985 |
| EP | 0236610 | 9/1987 |
| EP | 0263147 B1 | 4/1988 |
| EP | 0518445 A1 | 12/1992 |
| EP | 0500387 B1 | 7/1999 |
| EP | 0939773 | 9/1999 |
| EP | 0713527 B1 | 11/2001 |
| EP | 1230911 | 8/2002 |
| EP | 1237561 | 9/2002 |
| EP | 0693934 B1 | 10/2002 |
| EP | 0832198 B1 | 7/2003 |
| EP | 1331948 | 8/2003 |

(56) References Cited

FOREIGN PATENT DOCUMENTS

| | | |
|---|---|---|
| EP | 1358893 | 11/2003 |
| EP | 1373452 | 1/2004 |
| EP | 1496951 | 1/2005 |
| EP | 1515734 | 3/2005 |
| EP | 1551756 | 7/2005 |
| EP | 1631328 | 3/2006 |
| EP | 1631667 | 3/2006 |
| EP | 1656914 | 5/2006 |
| EP | 1677811 | 7/2006 |
| EP | 1693073 | 8/2006 |
| EP | 0923939 B1 | 6/2007 |
| EP | 1852017 | 11/2007 |
| EP | 1884253 | 2/2008 |
| EP | 1893187 | 3/2008 |
| EP | 1942851 | 7/2008 |
| EP | 1988909 | 11/2008 |
| EP | 2016187 | 1/2009 |
| EP | 2040669 | 4/2009 |
| EP | 2068949 | 6/2009 |
| EP | 2077864 | 7/2009 |
| EP | 2120561 | 11/2009 |
| EP | 2120851 | 11/2009 |
| EP | 2175864 | 4/2010 |
| EP | 2276484 | 1/2011 |
| EP | 2276505 | 1/2011 |
| EP | 2300047 | 3/2011 |
| EP | 2310056 | 4/2011 |
| EP | 2344170 | 7/2011 |
| EP | 2359784 | 8/2011 |
| EP | 2367443 | 9/2011 |
| EP | 2367444 | 9/2011 |
| EP | 2403938 | 1/2012 |
| EP | 2482772 | 8/2012 |
| EP | 2506824 | 10/2012 |
| EP | 2510944 | 10/2012 |
| EP | 2547371 | 1/2013 |
| EP | 2563736 | 3/2013 |
| EP | 2611453 | 7/2013 |
| EP | 2696890 | 2/2014 |
| EP | 2721933 | 4/2014 |
| EP | 2732601 A2 | 5/2014 |
| EP | 2801257 | 11/2014 |
| EP | 2809363 | 12/2014 |
| EP | 2943252 | 11/2015 |
| EP | 2296693 B1 | 12/2015 |
| EP | 3038631 | 7/2016 |
| EP | 3046522 | 7/2016 |
| EP | 3046523 | 7/2016 |
| EP | 3245871 | 11/2017 |
| FR | 2899064 | 10/2007 |
| FR | 3020758 | 11/2015 |
| GB | 736685 | 9/1955 |
| GB | 2391809 | 2/2004 |
| GB | 2432790 | 6/2007 |
| GB | 2435426 | 8/2007 |
| GB | 2484319 | 4/2012 |
| GB | 2540054 | 1/2017 |
| GB | 2540130 | 1/2017 |
| GB | 2547402 | 8/2017 |
| JP | 05-504567 | 7/1993 |
| JP | 62213754 | 3/1997 |
| JP | 2000509367 | 7/2000 |
| JP | 2008501361 | 1/2008 |
| JP | 2010532788 | 10/2010 |
| JP | 2012006971 | 1/2012 |
| JP | 2012162621 | 8/2012 |
| JP | 2012162621 A | 8/2012 |
| JP | 2013513608 | 4/2013 |
| NZ | 582246 | 7/2011 |
| PL | 399790 | 8/2016 |
| RO | 122644 | 10/2009 |
| RU | 2447880 C2 | 4/2012 |
| RU | 2480018 C2 | 4/2013 |
| UA | 117416 | 7/2018 |
| WO | WO 1988/002600 | 4/1988 |
| WO | WO 1992/011042 | 7/1992 |
| WO | WO 1992/014484 A1 | 9/1992 |
| WO | WO 1992/022221 | 12/1992 |
| WO | WO 1992022221 | 12/1992 |
| WO | WO 1994/005252 | 3/1994 |
| WO | WO 1994/023742 A1 | 10/1994 |
| WO | WO 1995/004135 A1 | 2/1995 |
| WO | WO 1996/038548 | 12/1996 |
| WO | WO 1997/044008 | 11/1997 |
| WO | WO 1998/022513 | 5/1998 |
| WO | WO 1999/022597 | 5/1999 |
| WO | WO 2001/028600 | 4/2001 |
| WO | WO 2002/000296 | 1/2002 |
| WO | WO 2001/041776 | 2/2002 |
| WO | WO 2002/030467 | 4/2002 |
| WO | WO 2003/047642 | 6/2003 |
| WO | WO 2003/080109 | 10/2003 |
| WO | WO 2003/090800 | 11/2003 |
| WO | WO 2003/106333 | 12/2003 |
| WO | WO 2004/093569 | 11/2004 |
| WO | WO 2004/108176 | 12/2004 |
| WO | WO 2005/034969 | 4/2005 |
| WO | WO 2007/045252 | 4/2007 |
| WO | WO 2007/134180 | 11/2007 |
| WO | WO 2007/137881 | 12/2007 |
| WO | WO 2008/041218 | 4/2008 |
| WO | WO 2008/049251 | 5/2008 |
| WO | WO 2008/049578 | 5/2008 |
| WO | WO 2008/064272 | 5/2008 |
| WO | WO 2008/103673 | 8/2008 |
| WO | WO 2009/116944 | 9/2009 |
| WO | WO 2009/118379 | 10/2009 |
| WO | WO 2009/137697 | 10/2009 |
| WO | WO 2009/147402 | 12/2009 |
| WO | WO 2010/044042 | 4/2010 |
| WO | WO 2010/082846 | 7/2010 |
| WO | WO 2010/101844 | 9/2010 |
| WO | WO 2011/028965 | 3/2011 |
| WO | WO 2011/068514 | 6/2011 |
| WO | WO 2011/113436 | 9/2011 |
| WO | WO 2011/126384 | 10/2011 |
| WO | WO 2011/139168 | 11/2011 |
| WO | WO 2012/030231 | 3/2012 |
| WO | WO 2012/052425 | 4/2012 |
| WO | WO 2012/140272 | 10/2012 |
| WO | WO 2013/009910 | 1/2013 |
| WO | WO 2013/113906 | 8/2013 |
| WO | WO 2013/172468 | 11/2013 |
| WO | WO 2014/110580 | 7/2014 |
| WO | WO 2015/030609 | 3/2015 |
| WO | WO 2015/041835 | 3/2015 |
| WO | WO 2015/041836 | 3/2015 |
| WO | WO 2015/074159 | 5/2015 |
| WO | WO 2007/045931 | 11/2015 |
| WO | WO 2015/166197 | 11/2015 |
| WO | WO 2015/173002 | 11/2015 |
| WO | WO 2015/173522 | 11/2015 |
| WO | WO 2015166197 | 11/2015 |
| WO | WO 2016/007776 | 1/2016 |
| WO | WO 2016/011498 | 1/2016 |
| WO | WO 2016/022670 | 2/2016 |
| WO | WO 2016/083798 | 6/2016 |
| WO | WO 2016/123539 | 8/2016 |
| WO | WO 2016/124926 | 8/2016 |
| WO | WO 2016/189113 | 12/2016 |
| WO | WO 2017/013448 | 1/2017 |
| WO | WO 2017/042568 | 3/2017 |
| WO | WO 2017/071663 | 5/2017 |
| WO | WO 2017/178822 | 10/2017 |
| WO | WO 2018/029698 | 2/2018 |
| WO | WO 2018/029705 | 2/2018 |
| WO | WO 2018/065608 | 4/2018 |
| WO | WO 2018/065789 | 4/2018 |
| WO | WO 2007/051599 | 6/2018 |

(56) References Cited

OTHER PUBLICATIONS

Timmons; "Oxyzyme(TM) sterile wound dressing: a new concept for wound healing"; Wounds UK, The Use of Oxyzyme sterile wound dressing with iodine on hard-to-heal wounds: Case study series; 15 pages (2007).
Artemuk, et al.; "Fermenty"; Institution of Education "Brest State University Named After A.S. Pushkin" Department of Chemistry; pp. 7-15 (2010).
Davydova, et al.; "Stability and Catalytic Properties Glucosooxidase From Penicillium Funiculosum G-15"; Vestnik Moscovskogo Universiteta. ser. 2. Khimiya. vol. 43. No. 6, pp. 366-370 (2002).
Tyzhigirova; "Quality indicators and analysis features of solutions"; Handbock, Irkutsk, Moscow State Medical University, pp. 5-15 (2016).
Xie; "The Antibacterial Activity of Honey and Its Application in the Medicine"; Strait Pharmaceutical Journal; vol. 16, No. 4, pp. 145-147 (Aug. 30, 2004).
Molan; "The Antibacterial Activity of Honey 2. Variation in the potency of the antibacterial activity"; Bee World; vol. 73, pp. 59-76 (1992).
Morgulis; "Studies on the Inactivation of Catalase. II. Inactivation by Ultra-Violet Radiation at Different Hydrogen ion Concentrations"; Journal of Biological Chemistry; vol. LXXXVI, pp. 75-85 (1930).
Nijhuis, et al.; "A randomized trial of honey barrier cream versus zinc oxide ointment"; British Journal of Nursing; vol. 21, No. 20, pp. S23-S24 (2012).
2015 Wounds UK Annual Conference—Nov. 9, 2015.
A. Doria, M.Zen, S. Bettio, M. Gatto, N. Bassi, L. Nalotto, A. Ghirardello, L. Iaccarino, L. Punzi: Autoimmunity Reviews journal homepage: Elsevier: Autoinflammation and autoimmunity: Bridging the divide (2012).
A. Gholipour Kanani et al: Effect of changing solvents on Poly(Caprolactone) Nanofibrous Webs Morphology. Journal of Nanomaterials. vol. 2011, Jan. 1, 2011 pp. 1-10.
Al-Waili et al., J. Medic Food, 14(10):1079-1096 (2011).
Anonymous "Gamma Ray" Wikipedia Sep. 22, 2016 retrieved from the internet on Dec. 5, 2017 (whole document).
Antibiotic-sparing wound gel shows real promise in fighting biofilm infection—Nov. 17, 2017.
Arne, Simon et al: Medical Honey for wound care—still the latest resort? Advance access publication Jan. 7, 2008.
Bang et al., the effect of dilution on the rate of hydrogen peroxide production in honey and its implications for wound healing, The Journal of Alternative and complementary medicine, vol. 9, p. 267-273 (2003).
BBC & ITV—Surgihoney—Feb. 24, 2014.
BBC Nature—When will we take medicinal honey seriously?—Jul. 22, 2014.
BBC South Today—Effects of Surgihoney and its effectiveness against infections found in soft tissue wounds, including multi resistant bacteria like MRSA and *E-coli*—Aug. 20, 2013.
Benjamin A Minden-Birkenmaier et al: Preliminary Investigation and Characterization of Electrospun Polycaprolactone and Manuka Honey Scaffolds for Dermal Repair. Journal of Engineered Fibers and Fabrics Jan. 1, 2015, pp. 4-2015.
Biofilm bacteria. The marshall protocol knowledge base May 5, 2015.
Biovert™ Enzyme & Substrate (patented) A two-part natural protection system, Dec. 1, 2014, pp. 1-2. Retrieved from internet, http://dewolfchem.com/wp-content/uploads/2014/12/2014_12_Biovert_SLS_lowres.pdf.
British Journal of Nursing—Reactive Oxygen: a new solution to antimicrobial resistance—2016.
Cimolai et al., BC Medic J., 49(2): 64-67 (2007).
Clarke L (2018)—The evaluation of SurgihoneyRO™ in the treatment of chronic wounds with suspected biofilms (Poster).
Clinical Review: Properties of honey: its mode of action and clinical outcomes. Jackie Stephen Haynes, Rosie Callaghan. Wounds UK, 2011, vol. 7, No. 1.
Cook et al. Curr Opin Infect Dis 2014, 27:125-129—Apr. 2014.
Cook et. al BMC Research Notes—The antimicrobial activity of prototype modified honeys that generate reactive oxygen species (ROS) hydrogen peroxide—2015.
Cooke Jonathan et al: The antimicrobial activity of prototype modified honeys that generate reactive oxygen species (ROS) hydrogen peroxide. vol. 8, 20, 2014, pp. 1-5.
Daily Mail—Doctors discover 'super honey' with amazing power to treat soldiers' wounds and kill superbug infections—Aug. 10, 2013.
Daily Mirror—'Miracle' honey that can prevent limb amputation with bacteria-killing properties—Apr. 25, 2016.
Dipjyoti Saha—Suvendu Bhattacharya: Hydrocolloids as thickening and gelling agents in food: a critical review published Nov. 6, 2010.
Doctor treats remote tribe in Papua, Indonesian New Guinea Jan. 30, 2017.
Dryden—Int J Antimicrob Agents. Mar. 2018;51(3):299-303—Reactive oxygen species: a novel antimicrobial.
Dryden et al. Hot Topics in Reactive Oxygen therapy: antimicrobial and immunological mechanisms, safety, and clinical applications. J Glob Antib Res. Feb. 17, 2017. pii: S2213-7165(17)30024-3.
Dryden et al. British Journal of Midwifery—Using antimicrobial Surgihoney to prevent caesarean wound infection—Jan. 2014, vol. 22, No. 1.
Dryden et al. Journal of Wound Care—A multi-centre clinical evaluation of reactive oxygen topical wound gel in 114 wounds.—Mar. 3, 2016.
Dryden et al., Infection prevention in wounds with Surgihoney, Journal of Hospital Infection (2014).
Dryden et. al. Surgihoney—Modified honey wound treatment: first report of in vitro activity and early clinical evaluation—Nov. 21, 2013.
Dryden M et al. Engineered Honey to Manage Bacterial Bioburden and Biofilm in Chronic Wounds, EWMA Free Paper Session: Infections and Antimicrobials (2015).
Dryden M et al: "Engineered honey: In vitro antimicobial activity of a novel topical wound care treatment", Journal of Global Antimicrobial Resistance September Elsevier Ltd GBR, vol. 2, No. 3, Sep. 2014 (Sep. 2014), pp. 168-172, ISSN: 2213-7165.
Dryden M Reactive oxygen species treatment in the management of wounds. Wounds UK 2017 vol. 13 No. 2 26-33.
Dryden, M. and Stephens, C., Wounds UK, 2018, 14—Reactive Oxygen® Made Easy.
Dryden. Reactive Oxygen therapy: a novel therapy in soft tissue infection. Current Opinion in Infectious Disease Apr. 2017; 30(2):143-149. doi:10.1097/QCO.0000000000000350.
Dunnill C, Patton T, Brennan J, et al. Reactive oxygen species (ROS) and wound healing: the functional role of ROS and emerging ROS-modulating technologies for augmentation of the healing process. Int Wound J 2015.
Dunnill et al. International Wound Journal—Reactive Oxygen Species (ROS) and wound healing: the functional role of ROS and emerging ROS-modulating technologies for the implementation of the healing process—Feb. 2017.
E. Mele: Electrospinning of natural polymers for advanced wound care: towards responsive and adaptive dressings. Journal of Materials Chemistry B, vol. 4, No. 28, Jan. 1, 2016.
English language translation of Japanese OA dated Feb. 4, 2019 (JP App No. 2016-565373).
English translation of Notice of Reasons for Rejection dated Jul. 24, 2018 on JP App 2016-565373.
Esposito et al. International Journal of Antimicrobial Agents—The diagnosis and management of skin infections—Jul. 2016.
Fenella Halstead, Beryl Oppenheim, Matthew Dryden: The in vitro antibacterial activity of engineered honey (surgihoney) against important biofilm-forming burn wound pathogens Nov. 23, 2014.
Fengjun Sun, Feng Qu et al. Biofilm-Associated infections May 5, 2015.
Filipini, R, (Poster), 2019—H202 (SurgihoneyRO™)—Fast healing autolytic debridement and healing in long standing infected chronic wounds.
Guardian—Why 'super honey' is the bees' knees for wounds and infections—Jan. 1, 2014.

(56) References Cited

OTHER PUBLICATIONS

Hall TJ, Blair JMA, Moakes RJA, Pelan EG, Grover LM, Cox SC. Antimicrobial emulsions: Formulation of a triggered release reactive oxygen delivery system. Materials science & engineering C, Materials for biological applications 2019;103:109735.
Halstead et. al.—Poster—The in vitro antibacterial activity of engineered honey (Surgihoney) against important biofilm-forming burn wound pathogens.—Apr. 25, 2015.
Halstead et. al. Journal of Wound Care—In vitro activity of an engineered honey, medical-grade honeys and antimicrobial wound dressings against biofilm-producing clinical bacterial isolates—Feb. 2, 2016.
Halstead et al. J Wound Care. Aug. 2, 2017;26(8):442-450—Use of an engineered honey to eradicate preformed biofilms of important wound pathogens: an in vitro study.
Hampshire Chronicle—Roger Backhouse QC hails pioneering honey for fighting bacteria that threatened his life—May 6, 2016.
Hampshire Chronicle—Ex-soldier Ben Steele to play 'murderball' for his country—Sep. 11, 2014.
Hampshire Chronicle—Honey has golden touch in beating bacteria—Jul. 11, 2013.
Hampshire Chronicle—Man of Steel won't let disability stop him in his tracks—Sep. 1, 2013.
Heyes et al. Surgihoney: Biotechnological honey wound treatment: first clinical report of its use in the tropics—Mar. 14, 2013.
Hudgell et al. Poster Wounds UK—Healing challenging wounds with SurgihoneyRO—a novel antimicrobial wound gel with antibiofiim action—Nov. 15, 2017.
Irish Times—The bee's knees for wounds and infections—Jul. 5, 2016.
Isao Tsunoda C Fragrance Journal, 2002, vol. 30.
January Reactive Oxygen e-newsletter—Jan. 2017.
Jeffrey B. Lyczak et al. Lung infections associated with cystic fibrosis. vol. 15, No. 2 (Apr. 2002).
Jeffrey D. Suh, David W. Kennedy. Treatment options for chronic rhinosinusitis—2011.
Jonathan Cooke et al: The antimicrobial activity of prototype modified honeys that generate reactive oxygen species (ROS) hydrogen peroxide. vol. 8, No. 1 Jan. 28, 2015.
Journal of Global Antimicrobial Resistance: Reactive oxygen: a novel antimicrobial mechanism for targetting biofilm-associated infection Feb. 20, 2017.
Journal of Wound Care—The use of Surgihoney to prevent or eradicate bacterial colonisation in dressing oncology long vascular lines.—Dryden et al. Journal of Wound Care vol. 23 , No. 6 , Jun. 2014.
Jull et al., The Cochrane Collaboration (2009).
July Reactive Oxygen e-newsletter—Jul. 2016.
June Reactive Oxygen e-newsletter—Jun. 2016.
Khan & Jones Journal of Trauma & Orthopaedics—Debridement Defining Something We Do—Mar. 2016.
Kretavicius et al., Inactivation of glucose oxidase during heat-treatment de-crystallization of honey, vol. 94, p. 115-122 (2010).
Kwakman P H S et al: "Antibacterial components of honey", IUBMB, Taylor and Francis, London, GB, vol. 64, No. 1, Jan. 1, 2012, pp. 48-55.
Liliana Liverani et al: Frontiers Electrospinning with benign solvents: feasibility study and versatile use of poly (epsilon-caprolactone) fibers, Mar. 30, 2016.
Lipsky et al. Journal of Antimicrobial Chemotherapy—Antimicrobial Stewardship in Wound Care—Jul. 25, 2016.
Longevity Bulletin From the Institute and Faculty of Actuaries—May 2016.
Lu J et al, Plos One (Feb. 2013) vol. 8 No. 2 e55898.
Lynne M. Bang et al., Journal of Alternative and Complementary Medicine, vol. 9, No. 2, Apr. 1, 2003.
Management and treatment of common infections Antibiotic guidance for primary care: For consultation and local adaptation (See p. 66 for SurgihoneyRO™ recommendation)—Public Health England, Public Health England, Sep. 2017.
Manisha Deb Mandal et al: asian pacific journal of tropical biomedicine: honey: its medicinal property and antibacterial activity 2011.
Matthew Dryden—reactive oxygen—a solution for healing and antimicrobial resistance 2015—Aug. 1, 2015.
Medical Independent—SurgihoneyRO & Sinusitis—May 27, 2016.
Miravittles et al. Int. J. Mol. Sci. 2017, 18(7), 1344—Chronic Respiratory Infection in Patients with Chronic Obstructive Pulmonary Disease: What Is the Role of Antibiotics?
Molan P C: The antibacterial activity of honey 1. The nature of the antibacterial activity. Bee world, bee research association. vol. 1-2, Jan. 1, 1992 pp. 5-29.
Mr Ali A Salamat surgihoney treatment of CRS-associated S. aureus biofilms May 13, 2015.
N. Høiby, T. Bjarnsholt, C. Moser, G. L. Bassi, T. Coenye, G. Donelli, L. Hall-Stoodley, V. Holá, C. Imbert, K. Kirketerp-Møller, D. Lebeaux, A. Oliver, A.J. Ullmann and C. Williams: ESCMID Guidelines: ESCMID guideline for the diagnosis and treatment of biofilm infections 2014. for the ESCMID Study Group for Biofilms (ESGB) and Consulting External Expert Werner Zimmerli.
Nasal irrigation wikipedia May 14, 2015.
NeilMed pharmaceuticals—sinus rinse isotonic May 14, 2015.
Newby RS et al. J Clin Pathol. Jun. 2018;71(6):554-558 Antimicrobial activity of a novel bioengineered honey against non-typeable Haemophilus influenzae biofilms: an in vitro study.
Nijhuis: Medihoney barrier cream Nov. 15, 2013 XP055305245.
November Reactive Oxygen e-news—Nov. 2016.
Nursing Standard—Healing Powers—Sep. 24, 2014.
Nursing Times—The role of bioengineered honey in wound care—Oct. 10, 2016.
October Reactive Oxygen e-newsletter—Oct. 2016.
P. Furrer, European Pharmaceutical Review, Apr. 18, 2013, Retrieved from the Internet URL http://www.europeanpharmaceuticalreivew.com/article/18434/thecentral-role-of-excipients-in-drug-formulation-2/.
Papadopoulou et al. Am J Rhinol Allergy. Jan. 2020;34(1)80-86.
Parker et al. International Journal of Surgery Protocols vol. 5, 2017, pp. 18-21—Impact of Surgihoney Reactive Oxygen on surgical site infection (SSI) after complex abdominal wall reconstruction (AWR) of grade 3 and 4 ventral Hernias: A single arm pilot study.
Paulus H S Kwakman et al: IUBMB Life 64(1) 48-55 Jan. 2012.
Paulus H. S. Kwakman et al: Two major medicinal honeys have different mechanisms of bacterial activity, vol. 6, No. 3 Mar. 4, 2011 p. e17709.
Politics First—Reactive Oxygen highlighted as potential breakthrough in battle against superbugs—Jan. 10, 2017.
Practical Clinical Pharmacy of Traditional Chinese Medicine, Zhu Yin-Long et al., Shanxi Science Technology Press, Jul. 2013, pp. 430-431.
Presentations from speakers—Apr. 13, 2016.
Prof. Paul Davis, John Wilkins: Oxyzyme: Oxygen, and its role in wound healing: a literature review (May 2007).
R Peter Manes, Pete S Batra. Etiology, Diagnosis and Management of Chronic Rhinosinusitis: Expert Rev Anti Infect Ther. 2013; 11(1):25-35.
Rachel B Cain, Devyani Lal Department of Otorhinolaryngology: Infection and Drug Resistance 2013:6 1-14.
RCT pilot study to compare Surgihoney RO with silver dressing in treatment of chronic bi-lateral vascular leg ulcers—Oct. 4, 2016.
Reactive Oxygen hailed in The Times as British breakthrough in war against antimicrobial resistance—Dec. 19, 2016.
Reactive Oxygen highlighted in House of Lords as new weapon to fight superbugs—Sep. 15, 2016.
Reactive Oxygen under the spotlight in House of Commons—Jul. 6, 2016.
Reactive Oxygen® research wins prestigious innovation award—Apr. 5, 2017.
Rev Biomed 1996; 7;43-49. Medical uses of honey. Amy E Jeffery, Carlos M. Echazarreta.
Role of bacterial biofilms. Centre for biological sciences May 5, 2015.

(56) References Cited

OTHER PUBLICATIONS

Rozaini Mohd Zohdi et al: Gelam Honey-based Hydrogel as burn wound dressing. Evidence-Based Complementary and Alternative Medicine. vol. 2012, Jan. 1, 2012 pp. 1-7.
Ruhl S. et al., Applied and Environmental Microbiology, Feb. 2011, p. 749-755.
S Bogdanov: "Characterisation of Antibacterial Substances in Honey" Lebensmittel Wissenschaft und Technologie, Jan. 1, 1984, pp. 74-76 retrieved from internet—http://www.bee-hexagon.net.files/file/fileE/Honey/Bogdanov_LWT_1984_sb.pfd.
Saeed at el. International Journal of Antimicrobial Agents—Prosthetic joints: shining light on challenging blind spots—Dec. 8, 2016.
Salamat et al; Development of an engineered honey (surgihoney) as a novel topical treatment—Jun. 5, 2017.
Shinnji Sugii, special edition Mitsubachi yurai genryo—sono genjou to ouyou no jissai (raw material from honey bee—its present state and actual application), Fragrance Journal vol. 30, No. 3 (2002).
Simona Sagona et al: Preliminary evaluation of glucose oxidase and it's products in vitro antimicrobial activities on Paenibacillus larvae ATCC9545 vegetative form. Bulletin of Insectology, Jan. 1, 2015 pp. 233-237. Retrieved from internet: www.bulletinofinsectology.org/pdfarticles/vol68-2015-233-237sagona.pdf.
Stephens, C., Wounds UK, 2019, (poster)—Clinical Evaluation of 54 Patients in the UK of a Bioengineered Reactive Oxygen® Wound Gel in the Treatment and Management of Wound Infection.
Suebsaeng et al.—Poster—Necrotising Fasciitis with multi-drug resistant colonisers—Oct. 6, 2016.
Surgery and Honey vol. 99 Issue: 2, Feb. 2017, pp. 52-55.
Surgihoney RO Featured at Wound Care Conference—Jan. 26, 2016.
Surgihoney RO helping patients in developing world—Jul. 25, 2016.
SurgihoneyRO™ officially recognised by NHS through Public Health England (PHE) guidance for common infections Oct. 11, 2017.
SurgihoneyTM in prestigious International Wound Journal—Jan. 6, 2016.
SurgihoneyTM showcased in Science Museum in London—Jul. 10, 2014.
The Times—Our brilliant biologists are changing the world—Dec. 19, 2016.
Thomas, H., Davies, L. and Westgate, S.J., Poster, Perfectus biomed, 2018—Treatment of World Health Organisation priority pathogens using an antimicrobial wound gel.
Tiina M et al: Antibacterial effect of the glucose oxidase-glucose system on food-poisioning organisms. International Journal of Food Microbiology, Elsevier BV, NL, vol. 8, No. 2, May 1, 1989, pp. 165-174.
UCLH pilot study on impact of SurgihoneyRO™ in preventing surgical site infection—Apr. 5, 2017.
University of Manchester—Honey's potential to save lives by destroying harmful fungus—Sep. 2, 2016.
University of Southampton—Could honey combat respiratory disease?—Apr. 29, 2016.
University of Southampton investigates potential benefits of Surgihoney in treating chronic rhinosinusitis—Jan. 5, 2016.
University researchers developing new Reactive Oxygen spray—Sep. 22, 2016.
US OA dated Feb. 26, 2019 (U.S. Appl. No. 15/528,969).

Vanesa Andreu et al: Smart dressings based on Nanostructured Fibers Containing Natural Origin Antimicrobial, Anti-Inflammatory, and Regenerative Compounds, vol. 8, Nov. 8, 2015, pp. 5154-5193.
Videos from Reactive Oxygen Symposium on Apr. 13, 2016.
Weston Roderick J: The contribution of catalase and other natural products to the antibacterial activity of honey: A review Food Chemistry, Elsevier Ltd, NL, vol. 71, No. 2, Nov. 1, 2000 (Nov. 1, 2000), pp. 235-239.
White JW, Subers MH, Schepartz AI. The identification of inibine, The antibacterial factor in honey as hydrogen peroxidase and its origin in a honey glucose oxidase system. Biochem. Biophys Act 1963; 73:57-70.
Williams et al.—Poster—honey as a novel antimicrobial coating in salvage revision total knee arthroplasty—poster presentation to 2015 European Bone & Joint Infection Society in Lisbon.
Winter The role of bioengineered honey in wound care. *Nursing Times*; 39 40: 15-17.—Oct. 18, 2016.
Woundcare4Heroes conference—Aug. 1, 2015.
Wounds UK—A patient's perspective on his military and civil post-trauma wound care treatment—2016.
XP-002762334—B.Behera et al: Colloids and surfaces B: Biointerfaces (2015).
Cooke; "When antibiotics can be avoided in skin inflammation and bacterial colonization: a review of topical treatments"; Curr Opin Infect Dis; vol. 27, No. 2, pp. 125-129 (Apr. 2014).
Elliott; "Doctors discover 'super honey' with amazing power to treat soldiers. Wounds and kill superbug infections"; MailOnline; 2 pgs (Aug. 10, 2013).
Lipsky et al.; "Antimicrobial sterwardship in wound care: a position paper from the British Society for antimicrobial chemotheraphy and European wound management assosication"; Journal of antimicrobial chemotherapy; vol. 71, pp. 3026-3035 (Jul. 25, 2016).
McNulty; Public Health England; Summary of antimicrobial prescribing guidance—managing common infections; pp. 1-107 (Oct. 2018).
Reactive Oxygen (RO): transforming wound care & infection control in an age of antimicrobial resistance; Elgar Concert Hall, Bramall music building, University of Birmingham, 102 pages (Apr. 13, 2016).
Research project: evaluation of the role of bacterial biofilms in the pathophysiology of chronic rhinosinusitis; centre for biological sciences, http://www.southampton.ac.uk/biosci/research/projects/role_of_bacterial_biofilms_in (1 pg) (May 5, 2015).
Sagona et al.; "Preliminary evaluation of glucose oxidase and its products in vitro antimicrobial activities on paenibacillus larvae ATCC9545 vegetative form"; Bulletin of Insectology; vol. 68, No. 2; pp. 233-237 (2015).
Tereos Syral; General Product Specification Meritose 200 Pharma; 3 pages (2014).
Tereos Syral; Safety Data Sheet Meritose 200 Pharma; 6 pages (2014).
Winter; "Prudent antibiotic stewardship in wound care management"; British journal of healthcare management; vol. 24, No. 4, pp. 170-171 (2018).
Winter; "Surgery and Honey"; vol. 99, No. 2; http://publishing.rcseng.ac.uk/doi/10.1308/rcsbull.2017.52; 7 pages (Feb. 2017).
Riswati, et al.; "Sugarcane bagasse for environmentally friendly superabsorbent polymer: synthesis methods and potential applications in oil industry"; IOP Conf. Series: Earth and Environmental Science; vol. 819, 7 pages (2021).
Sigma ("Glucose Oxidase from Aspergillus niger" retrieved from https://www.sigmaaldrich.com/US/en/product/sigma/g7141 on Jun. 20, 2023 (1 page).

\* cited by examiner

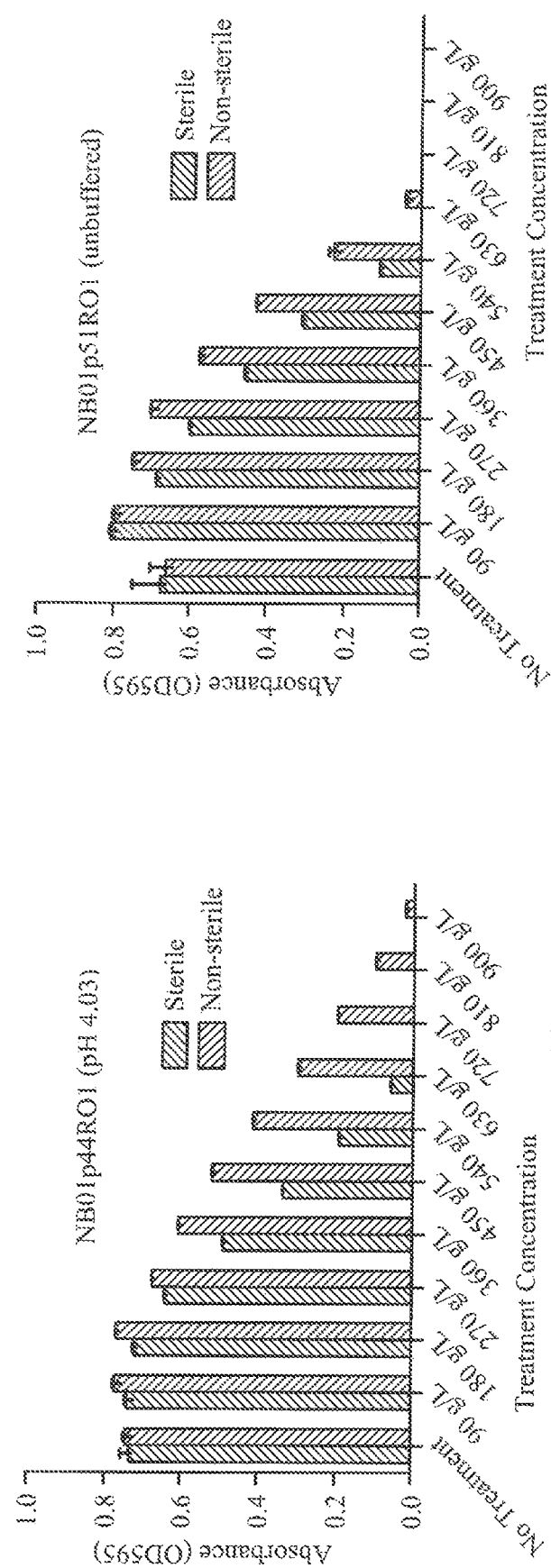
Figure 13
Figure 14
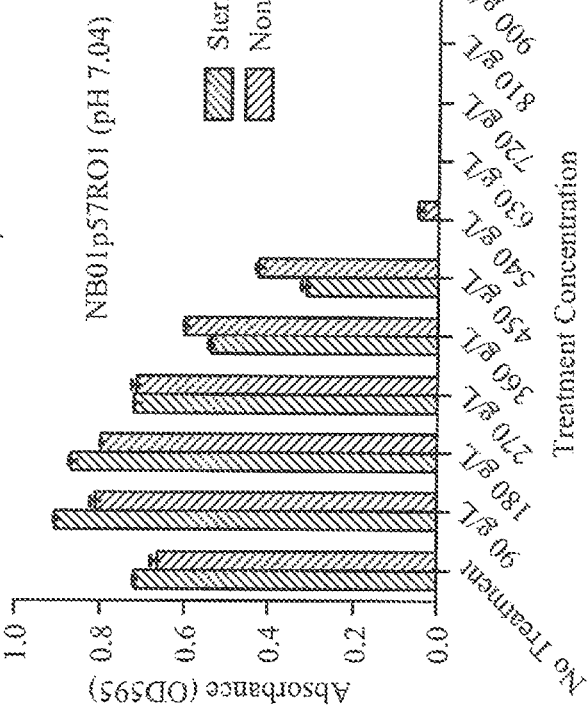
Figure 15

| | MIC | MBC |
|---|---|---|
| Surgihoney RO1 | 360 g/L | >900 g/L |
| NB01p44RO1 (non-sterile) | 900 g/L | >900 g/L |
| NB01p44RO1 (sterile) | 720 g/L | >900 g/L |
| NB01p51RO1 (non-sterile) | 630 g/L | >900 g/L |
| NB01p51RO1 (sterile) | 630 g/L | >900 g/L |
| NB01p57RO1 (non-sterile) | 540 g/L | 720 g/L |
| NB01p57RO1 (sterile) | 540 g/L | 540 g/L |

Figure 16

|  | MIC | | MBC | |
|---|---|---|---|---|
|  | Non-sterile | Sterile | Non-sterile | Sterile |
| SurgihoneyRO1 |  | 360 g/L |  | >900 g/L |
| SurgihoneyRO2 |  | 90 g/L |  | 90 g/L |
| NB01p43RO | >900 g/L | 720 g/L | >900 g/L | >900 g/L |
| NB01p51RO | >900 g/L | 810 g/L | >900 g/L | >900 g/L |
| NB01p57RO | >900 g/L | 810 g/L | >900 g/L | >900 g/L |
| NB01p44RO1 | 900 g/L | 720 g/L | >900 g/L | >900 g/L |
| NB01p51RO1 | 630 g/L | 630 g/L | >900 g/L | >900 g/L |
| NB01p57RO1 | 540 g/L | 540 g/L | 720 g/L | 540 g/L |
| NB01p44RO2 | 90 g/L | 270 g/L | 90 g/L | 270 g/L |
| NB01p51RO2 | 90 g/L | 180 g/L | 90 g/L | 180 g/L |
| NB01p57RO2 | 90 g/L | 270 g/L | 180 g/L | 270 g/L |

Figure 18

ANTIMICROBIAL SUPERABSORBENT COMPOSITIONS

CROSS-REFERENCE

This application is a national stage filing under 35 U.S.C. § 371 of PCT/GB2018/052976, filed Oct. 16, 2018, which claims the benefit of GB 1716986.3, filed Oct. 16, 2017, which applications are incorporated herein by reference in their entirety.

This invention relates to compositions for generating antimicrobial activity, particularly compositions that are able to generate hydrogen peroxide.

Honey has been used for treatment of microbial infections since ancient times. In recent years there has been a resurgence of interest in the therapeutic efficacy of honey, particularly in the area of wound healing. Clinical trials have shown that honey is an effective broad-spectrum antimicrobial agent which is effective against common wound-infecting organisms, such as *Pseudomonas aeruginosa, Staphylococcus aureus, Candida albicans* and *Escherichia coli*, and is effective against antibiotic-resistant strains of bacteria. As a natural product, honey also offers an attractive alternative to drug-based treatments.

Many different types of honey have antimicrobial activity. This activity is attributed largely to osmolarity, pH, hydrogen peroxide production and the presence of phytochemical components.

The applicant has appreciated that the antimicrobial effects of honey can be greatly enhanced and controlled by adding glucose oxidase to honey, and that compositions comprising honey and added glucose oxidase are applicable in the treatment of a number of infections, and notably in the treatment of infections caused by biofilms (see WO 2015/166197, WO 2016/083798 and WO 2016/124926). The applicant has also appreciated that beneficial effects may be afforded by compositions that produce low levels of hydrogen peroxide over an extended period of time, and which are storage-stable.

There is a continuing desire to provide antimicrobial products which are effective but also convenient, particularly in the field of wound care and infections, such as chronic and unresolved infections, and at surgical sites.

In a broad sense, the invention concerns hydrogen peroxide-generating compositions which comprise an enzyme that is able to convert a substrate to release hydrogen peroxide, and a substrate for the enzyme. Alternatively or additionally to the substrate, the composition may comprise a precursor-substrate that can be converted to a substrate for the enzyme. The invention also concerns such hydrogen peroxide-generating compositions comprising a water-absorbing component or material.

Preferably, the water-absorbing component is capable of forming a gel on contact with water. For example, the water-absorbing component may be a hydrophilic or hygroscopic powder. The water-absorbing component may be a polymer.

It is preferable that compositions of the invention do not comprise sufficient free water to enable the enzyme to convert the substrate.

According to the invention, there is provided a composition comprising an enzyme that is able to convert a substrate to release hydrogen peroxide, a substrate for the enzyme and a water-absorbing material or component, wherein the composition does not comprise sufficient free water to enable the enzyme to convert the substrate.

According to the invention, there is provided a composition comprising an enzyme that is able to convert a substrate to release hydrogen peroxide, a precursor-substrate that can be converted to a substrate for the enzyme, and a water-absorbing material or component, wherein the composition does not comprise sufficient free water to enable the precursor-substrate to be converted to the substrate or to allow the enzyme to convert the substrate.

In a particularly preferred embodiment, the composition is in the form of a powder.

According to the invention, there is provided a composition comprising an enzyme that is able to convert a substrate to release hydrogen peroxide, a substrate for the enzyme and a water-absorbing material or component, wherein the composition is in the form of a powder.

According to the invention, there is provided a composition comprising an enzyme that is able to convert a substrate to release hydrogen peroxide, a precursor-substrate that can be converted to a substrate for the enzyme, and a water-absorbing material or component, wherein the composition is in the form of a powder.

On contact with a fluid, such as wound exudate, the composition may absorb the fluid to form a gel, such as a hydrogel. The gel may produce hydrogen peroxide. As well as producing hydrogen peroxide, the gel may also provide a protective covering for a wound which may prevent or reduce the chance of infection and/or may assist healing. The gel may readily adhere to the wound and/or the tissue surrounding a wound. So, in effect, the gel may form a wound dressing that could be used alone or in conjunction with other dressing materials. The application of a powder may mean that fluid can be absorbed rapidly and a gel can form quickly, which may be particularly beneficial for treating wounds in the field, such as use by the military or the emergency services.

Preferably, the water-absorbing component has an absorption capacity or swelling capacity (which may also be termed free-absorbency capacity, free swelling capacity, fluid retention capacity or water-retention capacity) of 1 g of water, or aqueous solution, per gram of composition (i.e. 1 g/g), or higher. More preferably, the absorption capacity is 5 g/g, or higher. Even more preferably the absorption capacity is 10 g/g or higher. Typically, a superabsorbent material has an absorption capacity of at least 10 g/g. For example in some embodiments, the absorption capacity may be at least 15 g/g. In some embodiments, the absorption capacity may be at least 20 g/g. In some embodiments, the absorption capacity may be at least 30 g/g. In some embodiments, the absorption capacity may be at least 50 g/g. In some embodiments, the absorption capacity may be at least 100 g/g. In some embodiments, the absorption capacity may be at least 200 g/g. In some embodiments, the absorption capacity may be at least 500 g/g. In some embodiments, the absorption capacity may be at least 1000 g/g. Absorption capacity may also be termed centrifuge retention capacity.

The absorption capacity of a water-absorbing material can be measured by methods known to the skilled person.

In one method of measuring absorption capacity, the 'tea bag' method, an amount of the material is placed into a tea bag (acrylic/polyester gauze with fine meshes) and the bag is dipped in an excess amount of water or saline solution for one hour to reach equilibrium swelling. The excess solution is removed by hanging the bag until no more liquid drops off. The tea bag is then weighed and the swelling capacity is calculated as follows:

$$(W_1 - W_0)/W_0$$

$W_1$ is the weight of the swollen sample and $W_0$ is the original weight of the material.

Water-retention capacity may be measured in deionised water. Alternatively, water-retention capacity may be measured in a saline solution, such as a 0.9 wt % saline solution.

In another method to measure absorption capacity, the centrifuge method, 0.2 g ($W_1$), of the material is placed into a bag (60×60 mm) made of non-woven fabric. The bag is dipped in 100 mL of saline solution (0.9% by weight) for half an hour at room temperature. It is taken out, and then excess solution is removed by a centrifugal separator for 3 minutes at 250 g, then the weight of the bag ($W_2$) is measured. The same stages are carried out with an empty bag and the weight of the bag ($W_0$) is measured. The water-absorbing capacity is measured as follows:

$$(W_2 - W_0 - W_1)/W_1$$

This test (NWSP 241.0R2) is standardised by the European Disposables and Nonwovens Association (EDANA).

In a particularly preferred embodiment, the water-absorbing component is a superabsorbent material or component.

According to the invention, there is provided a composition comprising an enzyme that is able to convert a substrate to release hydrogen peroxide; a substrate for the enzyme; and a superabsorbent material or component.

According to the invention, there is provided a composition comprising an enzyme that is able to convert a substrate to release hydrogen peroxide; a substrate for the enzyme; and a superabsorbent material or component, wherein the composition is in the form of a powder.

According to the invention, there is provided a composition comprising an enzyme that is able to convert a substrate to release hydrogen peroxide; a precursor-substrate that can be converted to a substrate for the enzyme; and a superabsorbent material or component, wherein the composition is in the form of a powder.

The superabsorbent component may be a superabsorbent polymer (SAP). SAPs are polymers that can absorb and retain extremely large amounts of liquid relative to their own mass, SAPS are usually made from hydrophilic polymers containing anionic water-holding groups, such as carboxylic acid groups. Commonly, SAPs are produced from acrylic acid, its salts, or acrylamide. SAPs are preferably cross-linked, with the degree and type of cross-linking affecting its properties. For example, low-density cross-linked SAPs generally have higher water-retention capacity and swell to a larger degree, but may have a softer and stickier gel formation, High cross-link density polymers may exhibit lower water retention capacity, but may provide a firmer gel that is able to retain its shape more readily.

SAPs may be classified according to the charge in the cross-linked chains. For example, the SAP may be non-ionic, ionic, amphoteric or zwitterionic. In some preferred embodiments, the hydrogels are anionic.

Conventional SAPs useful for compositions according to the invention include polyacrylates and polyacrylamides, such as cross-linked polyacrylates and polyacrylamides. A particularly preferred SAP is sodium polyacrylate.

The SAP may be selected from the group consisting of: a hydrolysed cellulose-polyacrylonitrile; a starch-polyacrylonitrile co-polymer; a cross-linked co-polymer of maleic anhydride, such as ethylene maleic anhydride co-polymer; cross-linked carboxymethyl cellulose; polyvinyl alcohol co-polymer; and cross-linked polyethylene oxide.

Although synthetic polymer-based SAPs may be preferred, polysaccharide-bases SAPs and poly(amino acid)-based SAPs may also be used.

Compositions of the invention may comprise 0.5 to 75% by weight of the water-absorbing component (e.g. superabsorbent component). Compositions of the invention may comprise 1 to 50% by weight of the water-absorbing component. Compositions of the invention may comprise 2 to 30% by weight of the water-absorbing component. Compositions of the invention may comprise at least 0.5% by weight of the water-absorbing component. Compositions of the invention may comprise 50% by weight, or less, of water-absorbing component. Compositions of the invention may comprise 2% by weight, or more, of the water-absorbing component. Compositions of the invention may comprise 30% by weight, or less, of the water-absorbing component.

Compositions of the invention may comprise at least 10% by weight of the water-absorbing component. Compositions of the invention may comprise at least 25% by weight of the water-absorbing component. Compositions of the invention may comprise 75% by weight, or less of water-absorbing component. Compositions of the invention may comprise 25% to 75% by weight of the water-absorbing component.

If the composition is in the form of a powder, the particle size may be adjusted to optimise the composition according to its intended application. For example, the smaller the particle size, the more easily it may become solubilised or absorb fluid. However, it may be undesirable for the particle size to be too small such that a significant amount becomes aerosolised upon dispensing.

The powder may have a mean particle size of 3000 μm or less. The powder may have a mean particle size of 2000 μm or less. The powder may have a mean particle size of 1000 μm or less. The powder may have a mean particle diameter of 500 μm or less.

The powder may have a mean particle size of 50 μm or more. The powder may have a mean particle size of 100 μm or more. The powder may have a mean particle size of 200 μm or more.

For example, the powder may have a mean particle size of 50 to 3000 μm. The powder may have a mean particle size of 100 to 2000 μm. The powder may have a mean particle size of 100 to 1000 μm.

The powder may contains less than 10% of particles with a size of 1000 μm or more. The powder may contain less than 10% of particles with a size of 50 μm or less.

The powder may have a modal particle size of 3000 μm or less. The powder may have a modal particle size of 2000 μm or less. The powder may have a modal particle size of 1000 μm or less. The powder may have modal particle size of 500 μm or less.

The powder may have a modal particle size of 50 μm or more. The powder may have a modal particle size of 100 μm or more. The powder may have a modal particle size of 200 μm or more.

For example, the powder may have a modal particle size of 50 to 3000 μm. The powder may have a modal particle size of 100 to 2000 μm. The powder may have a modal particle size of 100 to 1000 μm.

Particle size is conventionally reported in terms of diameter irrespective of the actual particle shape; commonly the equivalent sphere diameter, defined by ISO 9276-1. Particle size analysis may be undertaken, for example, by image analysis using equivalent projected circle area or Feret diameters.

The powder may have a polymodal, (e.g. bimodal or trimodal) particle distribution.

The powder may have a peak sphericity of 0.8 or higher, 0.85 or higher or 0.9 or higher.

Compositions of the invention may comprise an unrefined substance that includes the substrate for the enzyme. The term "unrefined" is used herein to refer to substances that have not been processed into a pure form. Unrefined substances include substances that may have been concentrated, for example by drying or boiling. The substance may include one or more substrates from a natural source (termed herein a "natural substance"). Examples of natural substances include substances from a plant source, including from sap, roots, nectar, flowers, seeds, fruit, leaves, or shoots. The substance may be an unrefined natural substance, such as honey.

If compositions of the invention do comprise honey, the honey may be pasteurised. The honey may not contain catalase activity. The honey may be creamed. The honey may be a dried honey, such as a powdered honey.

In compositions of the invention that comprise honey, the honey may account for at least 10% by weight of the composition. In a more preferred embodiment, the honey many account for at least 25% by weight of the composition. In an even more preferred embodiment, the honey may account for at least 40% by weight of the composition. Honey may account for 10 to 80% by weight of the composition. For example, honey may account for 25 to 75% by weight of the composition.

Because honey is a natural product, its composition can vary greatly depending on its source. For example, the difference in antimicrobial potency among honeys can be more than one hundred-fold, depending on the geographical, seasonal and botanical source of the honey, as well as the harvesting, processing and storage conditions. Consequently, the antimicrobial efficacy may also vary depending on the type of honey used. Furthermore, honey may also contain other components, such as allergens e.g. trace amounts of pollen, which may cause adverse reactions when applied to certain subjects and make it unsuitable for certain pharmaceutical applications.

Honey may require processing such that it is in a suitable form for application to subjects, which can add cost and complexity to the production process. Such processing may include creaming or pasteurisation. Furthermore, for certain pharmaceutical applications, it may be difficult to get regulatory approval for honey-based compositions.

Consequently, although compositions based on natural products, such as honey-based compositions, may be used in compositions of the invention, there is a desire to provide improved compositions which provide some of the antimicrobial benefits provided by honey, but which also overcome some of its disadvantages.

So, the invention also concerns compositions that do not comprise an unrefined natural substance such as honey. For example, the compositions of the invention may comprise a purified enzyme that is able to convert a substrate to release hydrogen peroxide; and a purified substrate for the enzyme (or a purified precursor substrate that can be converted to a substrate for the enzyme).

Surprisingly, the applicant has found that compositions comprising a purified enzyme and a purified substrate or purified precursor-substrate can be more effective at killing microorganisms than known honey-based compositions that can generate hydrogen peroxide.

Consequently, according to the invention, there is provided a composition for generating hydrogen peroxide comprising: a purified enzyme that is able to convert a substrate to release hydrogen peroxide; a purified substrate for the enzyme; and a superabsorbent component.

According to the invention, there is provided a composition for generating hydrogen peroxide comprising: a purified enzyme that is able to convert a substrate to release hydrogen peroxide; a purified substrate for the enzyme; and a superabsorbent component, wherein the composition is in the form of a powder.

According to the invention, there is provided a composition for generating hydrogen peroxide comprising: a purified enzyme that is able to convert a substrate to release hydrogen peroxide; a purified precursor-substrate that can be converted to a substrate for the enzyme; and a superabsorbent component.

According to the invention, there is provided a composition for generating hydrogen peroxide comprising: a purified enzyme that is able to convert a substrate to release hydrogen peroxide; a purified precursor-substrate that can be converted to a substrate for the enzyme; and a superabsorbent component, wherein the composition is in the form of a powder.

Preferably, the enzyme is an oxidoreductase enzyme. Examples of oxidoreductase enzymes that can convert a substrate to release hydrogen peroxide include glucose oxidase, hexose oxidase, cholesterol oxidase, galactose oxidase, pyranose oxidase, choline oxidase, pyruvate oxidase, glycollate oxidase, and amioacid oxidase. The corresponding substrates for these oxidoreductase enzymes are D-glucose, hexose, cholesterol, D-galactose, pyranose, choline, pyruvate, glycollate and aminoacid, respectively.

A mixture of one or more oxidoreductase enzymes and one or more substrates for the oxidoreductase enzymes may be present in a composition of the invention.

According to a preferred embodiment of the invention, the oxidoreductase enzyme is glucose oxidase and the substrate is D-glucose.

References herein to "enzyme" refer to one or more enzyme. For example, in some embodiments, compositions of the invention may comprise a plurality of enzymes that are able to convert a substrate to release hydrogen peroxide. In some embodiments, compositions of the invention may comprise only one enzyme that is able to convert a substrate to release hydrogen peroxide.

The term "purified enzyme" is used herein to include an enzyme preparation in which the enzyme has been separated from at least some of the impurities originally present when the enzyme was produced. Preferably, impurities that have been removed or reduced include those that would otherwise interfere with the ability of the enzyme to convert the substrate to release hydrogen peroxide.

It may not always be necessary or desirable that the purified enzyme is at a high level of purity provided that the enzyme is able to convert the substrate to release hydrogen peroxide. In some circumstances, it may be desirable to use a relatively crude enzyme preparation. Examples of suitable purity levels include at least 10%, 20%, 30%, 40%, 50%, 60%, 70%, 80%, or 90% pure (mass purity). Preferably, the enzyme is at least 90% pure. Even more preferably, the enzyme is at least 99% pure.

The enzyme may have been produced by recombinant or non-recombinant means, and may be a recombinant or non-recombinant enzyme. The enzyme may be purified from a microbial source, preferably from a non-genetically modified microbe.

The level of purity of the enzyme may be selected as appropriate depending on the intended use of the composition. For medical use, a medical grade or medical device grade of purity may be used. For pharmaceutical use, a pharmaceutical grade of purity may be used.

Compositions of the invention may comprise sufficient enzyme and substrate to provide for sustained release of hydrogen peroxide at a specific level or concentration.

Compositions of the invention may comprise sufficient enzyme and substrate to provide for sustained release of hydrogen peroxide at a level of less than 2 mmol/litre for a period of at least twenty four hours, following dilution of the composition.

Compositions of the invention may comprise sufficient enzyme and substrate to provide for sustained release of at least 0.02, 0.03, 0.04, 0.05, 0.1, 0.2, 0.3, 0.4, 0.5, 1 or 1.5 mmol/litre hydrogen peroxide for a period of at least 24 hours, more preferably 48 hours.

So, in some embodiments, compositions of the invention may comprise sufficient enzyme and substrate to provide for sustained release of 0.1 to 2 mmol/litre hydrogen peroxide for a period of at least 24 hours, more preferably 48 hours.

For example, in some embodiments, compositions of the invention may provide for sustained release of hydrogen peroxide at a concentration of at least 2 ppm, at least 5 ppm, at least 10 ppm, at least 20 ppm or at least 50 ppm. In preferred embodiments, the level may be at least 2 ppm. In some embodiments, the concentration may be, at the most, 500 ppm, 200 ppm, 100 ppm, 50 ppm, 20 ppm or 10 ppm. In preferred embodiments, the level may be 20 ppm or less. In even more preferred embodiments, the level may be 10 ppm or less. For example, the concentration may be 10 to 500 ppm, 20 to 200 ppm or 50 to 100 ppm, 2 to 50 ppm, 2 to 20 ppm or 5 to 10 ppm. If the composition does not comprise sufficient free water to allow the enzyme to convert the substrate (e.g. if the composition is a dry or dried composition), hydrogen peroxide production may only occur once it has been diluted by water and there is sufficient free water to allow the enzyme to convert the substrate. Addition of water may thus initiate hydrogen peroxide production. Compositions, of the invention may provide for sustained release of hydrogen peroxide for at least 1 hour, at least 12 hours, at least 24 hours, at least 2 days, or at least 4 days. Preferably, the level of hydrogen peroxide is sustained for at least 4 days. In preferred embodiments, the level of hydrogen peroxide is sustained at 10 to 500 ppm for at least 1 hour, at least 12 hours, at least 24 hours, at least 2 days, or at least 4 days. In other embodiments, the level of hydrogen peroxide is sustained at 50 to 100 ppm for at least 1 hour, at least 12 hours, at least 24 hours, at least 2 days, or at least 4 days. In other embodiments, the level of hydrogen peroxide is sustained at 2 to 50 ppm for at least 12 hours, at least 24 hours, at least 2 days, or at least 4 days. In other embodiments, the level of hydrogen peroxide is sustained at 5 to 10 ppm for at least 12 hours, at least 24 hours, at least 2 days, or at least 4 days. In some embodiments, compositions of the invention may provide for sustained release of 2 to 500 ppm hydrogen peroxide for at least 24 hours.

Compositions of the invention may comprise 25 to 2000 ppm of the enzyme, for example 50 to 1000 ppm of the enzyme. Compositions of the invention may comprise 750 to 2000 ppm of the enzyme. Compositions of the invention may comprise at least 500 ppm of the enzyme. Compositions of the invention may comprise 250 to 1500 of the enzyme.

The enzyme activity (for example, the glucose oxidase activity) may range, for example, from 1-400 IU/mg, or 1-300 IU/mg, for example 250-280 IU/mg. The amount of enzyme used is likely to depend on several factors, including the desired use of the composition, the desired level of hydrogen peroxide release, and the desired length of time for hydrogen peroxide release. A suitable amount of enzyme can readily be determined by a person of ordinary skill in the art, if necessary using a well diffusion assay, to determine the extent of hydrogen peroxide release for different amounts of enzyme. Suitable amounts of enzyme (such as glucose oxidase) may be from 0.0001% to 0.5% w/w of the composition. The amount of enzyme used may be selected so as to produce a composition for generating antimicrobial activity that is equivalent to a selected phenol standard (for example a 10%, 20%, or 30% phenol standard).

Compositions of the invention may comprise at least 1 unit, and preferably up to 1500 units, of the enzyme per gram of the composition. A "unit" is defined herein as the amount of enzyme (e.g. glucose oxidase) causing the oxidation of 1 micromole of substrate (e.g. glucose) per minute at 25 degrees centigrade at pH 7.0.

In some embodiments, a composition according to the invention comprises more than 15 units, for example at least 30 units, at least 50 units, or at least 100 units, and suitably less than 685 units, for example 100-500 units, of enzyme (e.g. glucose oxidase) per gram of the composition.

In other embodiments of the invention, a composition according to the invention comprises at least 500 units, for example 500-1000 units, or 685-1000 units, of enzyme (e.g. glucose oxidase) per gram of the composition.

References herein to "substrate" or precursor-substrate" refer to one or more substrate. For example, in some embodiments, compositions of the invention may comprise a plurality of substrates or precursor-substrates. In some embodiments, compositions of the invention may comprise only one substrate or only one precursor substrate.

The term "purified substrate" or "purified precursor-substrate" is used herein to include a substrate or precursor-substrate preparation in which the substrate or precursor-substrate has been separated from at least some of the impurities originally present when the substrate or precursor-substrate was obtained or produced. The purified substrate or precursor-substrate may be obtained from a natural source or may be synthetically produced. The purified substrate or precursor-substrate may be a processed, extracted, or refined substrate or precursor-substrate (i.e. a substrate or precursor-substrate in which impurities or unwanted elements have been removed by processing).

It may not always be necessary or desirable that the purified substrate or precursor substrate is at a high level of purity provided that the enzyme is able to convert the substrate to release hydrogen peroxide. In some circumstances, it may be desirable to use a relatively crude substrate or precursor-substrate preparation. Examples of suitable purity levels include at least 10%, 20%, 30%, 40%, 50%, 60%, 70%, 80%, 90%, 95%, or 99% pure. Preferably the purity level is at least 90%, even more preferably at least 99%. However, in some embodiments, it may be desirable that the purified substrate or purified precursor-substrate is a medical grade, medical device grade, or pharmaceutical grade substrate or precursor-substrate.

In particular embodiments, the purified substrate or precursor substrate is or comprises a purified sugar. The term "sugar" is used herein to refer to a carbohydrate with the general formula $C_m(H_2O)_n$. The purified sugar may be obtained from a natural source (for example a processed, extracted, or refined natural sugar), or be synthetically produced. The purified sugar may be at least 10%, 20%, 30%, 40%, 50%, 60%, 70%, 80%, 90%, 95%, or 99% pure. Preferably, the purity level is at least 90%. Even more preferably the purity level is at least 99%. The purified sugar may be a medical grade, medical device grade, or pharmaceutical grade sugar. The sugar may include, for example purified D-glucose, hexose, or D-galactose. For example, the purified sugar may be medical grade, medical device grade, or pharmaceutical grade D-glucose, hexose, or D-galactose.

In particular embodiments, the enzyme and the substrate are purified, for example purified glucose oxidase and purified D-glucose, suitably medical grade, medical device grade, or pharmaceutical grade glucose oxidase and D-glucose.

For compositions of the invention which comprise a precursor-substrate, the composition preferably comprises one or more enzymes (preferably purified enzymes) for converting the precursor-substrate to the substrate for the enzyme. However, in some embodiments, the precursor-substrate may not necessarily be converted to the substrate enzymatically. For example, for some precursor substrates, addition of water may be sufficient for conversion. Alternatively or additionally, compositions of the invention may comprise non-enzymatic catalysts.

So, compositions of the invention which comprise a precursor-substrate may comprise a first enzyme that is able to convert the substrate to release hydrogen peroxide, and a second enzyme that is able to convert the precursor-substrate to the substrate for the first enzyme.

The precursor-substrate is preferably a carbohydrate, such as a polysaccharide, or a sugar e.g. a disaccharide, or sugar derivative.

For example, the precursor-substrate may be sucrose, the first enzyme may be glucose oxidase and the second enzyme may be invertase.

In another example, the precursor-substrate may be maltose, the first enzyme may be glucose oxidase and the second enzyme may be maltase.

Compositions of the invention which comprise a precursor-substrate may comprise an enzyme (preferably a purified enzyme) that is able to convert the substrate to release hydrogen peroxide, and at least two enzymes (e.g. second and third enzymes, preferably purified enzymes) that are able to convert the precursor-substrate to the substrate for the first enzyme.

For example, the precursor-substrate may be starch, the first enzyme may be glucose oxidase and the second and third enzymes may be amylase and maltase.

For example, the precursor-substrate may be cellulose, the first enzyme may be glucose oxidase and the second and third enzymes may be cellulose and beta-glucosidase.

In some embodiments, compositions of the invention may comprise both a substrate that can be converted by the enzyme to generate hydrogen peroxide, and a precursor-substrate that can be converted to the substrate.

Although compositions of the invention preferably do not include sufficient free water to allow the enzyme to convert the substrate, in some embodiments, compositions of the invention may comprise sufficient free water to allow the enzyme to convert the substrate.

Compositions of the invention may comprise freeze-drying protective agents. This is because compositions of the invention can be formed by freeze-drying. Preferably, the freeze-drying protective agent is a sugar or polysaccharide. In some embodiments the freeze-drying protective agent comprises cyclodextrin (e.g. methylated β-cyclodextrin) and/or maltodextrin. Other suitable freeze-drying protective agents may include polyethylene glycol, dextran, hydroxyethyl starch, ficoll, gum Arabic, gelatin, polyvinylpyrrolidone, cellulose, methocel, sepadex or bovine serum albumin.

If compositions of the invention comprise a freeze-drying protective agent, the freeze-drying protective agent may be present in an amount of 25 to 75% by weight, for example 30 to 60% by weight.

In one embodiment, a composition of the invention may comprise 25 to 75% by weight unrefined natural substrate (e.g. honey), 25 to 75% by weight freeze-drying protective agent and 2 to 25% superabsorbent component. For example, a composition of the invention may comprise 30 to 50% by weight unrefined natural substrate (e.g. honey), 30 to 50% by weight freeze-drying protective agent and 4 to 25% superabsorbent component.

In one embodiment, a composition of the invention may comprise 25 to 75% by weight sugars (e.g. glucose+fructose), 25 to 75% by weight freeze-drying protective agent and 2 to 25% superabsorbent component. For example, a composition of the invention may comprise 30 to 50% by weight sugars (e.g. glucose+fructose), 30 to 50% by weight freeze-drying protective agent and 4 to 25% superabsorbent component.

In one embodiment, a composition of the invention may comprise 25 to 75% by weight of substrate and solute combined (e.g. glucose+fructose), 25 to 75% by weight freeze-drying protective agent and 2 to 25% superabsorbent component. For example, a composition of the invention may comprise 30 to 50% by weight substrate and solute combined (e.g. glucose+fructose), 30 to 50% by weight freeze-drying protective agent and 4 to 25% superabsorbent component.

Compositions of the invention may not comprise a freeze-drying protective agent.

In one embodiment, a composition of the invention may comprise 50 to 95% by weight honey and 5 to 50% superabsorbent component.

In one embodiment, a composition of the invention may comprise 50 to 95% by weight sugars and 5 to 50% superabsorbent component.

In one embodiment, a composition of the invention may comprise 50 to 95% by weight substrate and solute combined, and 5 to 50% superabsorbent component.

Compositions of the invention may be storage-stable. The term "storage-stable" is used herein to mean that the composition can be stored at ambient temperature for at least several days, preferably at least a week, more preferably at least one or two months, whilst retaining the ability to generate antimicrobial activity following dilution of the composition. A preferred storage temperature is below 37° C., preferably 20-25° C. Preferably compositions are stored away from exposure to light.

Hydrogen peroxide is generally unstable at ambient temperature. The lack of sufficient free water in some compositions of the invention may thus prevent the enzyme converting the substrate to release hydrogen peroxide, and thus helps to maintain the stability of the composition for extended periods at ambient temperature. A composition of the invention may include some water provided that there is not sufficient free water to allow the enzyme to convert the substrate. Suitable amounts of water will vary depending on the precise components of the composition. However, typically, a storage-stable composition of the invention preferably comprises less than 20% (by weight) total water content, for example, 10%-19%, water. Compositions of the invention may comprise 12% or less (by weight) of water. Compositions of the invention may comprise 10% or less (by weight) of water. Compositions of the invention may comprise 5% or less (by weight) of water. Compositions of the invention may comprise 3% or less (by weight) of water. Compositions of the invention may comprise 1% or less (by weight) of water.

For compositions of the invention that do contain sufficient free water to allow the enzyme to convert the substrate, water may be present in an amount which is at least 20% by weight, or at least 30% by weight.

The skilled person would understand that if a composition of the invention does not comprise sufficient free water to allow the enzyme to convert the substrate, it may contain trace amounts of free water that may allow trace amounts, or substantially no, hydrogen peroxide to be produced. Hydrogen peroxide may be present in the composition at a concentration of 120 µM or less, preferably 100 µM or less, more preferably 80 µM or less. Once the composition is diluted, hydrogen peroxide may then be generated at substantial concentrations.

Preferably, compositions of the invention comprise substantially no hydrogen peroxide, trace amounts of hydrogen peroxide or no detectable hydrogen peroxide. For example, hydrogen peroxide is preferably not detectable using a hydrogen peroxide test strip, such as a Quantofix® peroxide test stick (Sigma Aldrich, UK). For example, hydrogen peroxide may present at a level less than 1 ppm or at a level less than 0.5 ppm. Hydrogen peroxide may be at a level less than 0.1 ppm.

Compositions of the invention may comprise an additional component which is preferably a solute. References herein to "solute" refer to one or more solute. For example, in some embodiments, compositions of the invention may comprise a plurality of solutes. In some embodiments, the composition may only comprise one solute. Preferably the solute is soluble in water.

The solute may be distinct from the substrate, or in some examples, the substrate may be same as the solute. For example, the composition may comprise fructose and fructose oxidase: the fructose being both the solute and the substrate for enzyme. In another example, the substrate may be glucose and the solute may be fructose.

The solute is preferably purified, meaning that the solute has been separated from at least some of the impurities originally present when the solute was obtained or produced. The purified solute may be obtained from a natural source or may be synthetically produced. The purified solute may be a processed, extracted, or refined substrate (i.e. a solute in which impurities or unwanted elements have been removed by processing).

It may not always be necessary or desirable that the purified solute is at a high level of purity. In some circumstances, it may be desirable to use a relatively crude solute preparation. Examples of suitable purity levels include at least 10%, 20%, 30%, 40%, 50%, 60%, 70%, 80%, 90%, 95%, or 99% pure. Preferably, the purity level is at least 90%. Even more preferably, the purity level is at least 99%. However, in some embodiments, it may be desirable that the solute is a medical grade, medical device grade, or pharmaceutical grade solute.

The solute may be a carbohydrate. The solute may be a polysaccharide. Preferably, the solute is a sugar or sugar derivative. More preferably, the solute is a sugar. Suitable sugars include oligosaccharides, disaccharides or monosaccharides. Preferably, the sugar is a disaccharide or a monosaccharide. In particularly preferred embodiments, the sugar is a monosaccharide. Suitable sugars may include fructose, glucose, galactose, sucrose and maltose. In a particularly preferred embodiment, the sugar is fructose.

The term "sugar derivative" is used herein to refer to a sugar that has been modified by addition of one or more substituents other than a hydroxyl group. Sugar derivatives, thus encompass amino sugars, acidic sugars, deoxy sugars, sugar alcohols, glycosylamines and sugar phosphates. For example, sugar derivatives may include glucose-6-phosphateglucosamine, glucoronate, gluconate, galactosamine, glucosamine, sialic acid, deoxyribosefucose, rhamnose glucuronic acid, polyols (e.g. sorbitol, erythritol, xylitol, mannitol, lactitol and maltitol) and sucralose.

Compositions of the invention may comprise two or more solutes, as described herein. For example, compositions of the invention may comprise two or more sugars or sugar derivatives. The composition may comprise a maximum of two solutes, e.g. two sugars or sugar derivatives; or a maximum of three solutes, e.g. three sugars or sugar derivatives. For instance, a composition of the invention may comprise glucose, fructose and sucrose.

The solute preferably has a high solubility in water, for example a solubility which is greater than glucose. Glucose has a solubility of 90 g/100 g water at 20° C. and 1 atm. In a preferred embodiment, the solute has a solubility greater than or equal to 100 g/100 g water at 20° C. and 1 atm, in a more preferred embodiment, the solute has a solubility greater than or equal to 200 g/100 g water at 20° C. and 1 atm, in an even more preferred embodiment, the solute has a solubility greater than 300 g/100 g water at 20° C. and 1 atm.

A solute with a high solubility may be advantageous because if the composition of the invention is a solution, it may enable the solution to have a high concentration of solutes, which may in turn provide a high osmolarity or osmotic strength. Compositions with a high osmolarity or osmotic strength may assist with the antimicrobial efficacy of the composition because they may reduce the amount of water available for microbes or draw water away from microbes, and may assist in wound healing and wound debridement.

Fructose is a particularly preferred solute because it has a solubility of about 375 g/100 g water at 20° C. and 1 atm. Consequently, the solute may be fructose.

In some embodiments, the solute with a solubility of at least 100 g/100 g water at 20° C. and 1 atm, at least 200 g/100 g water at 20° C. and 1 atm or at least 300 g/100 g water at 20° C. and 1 atm, may be the purified substrate. So, for example, a composition of the invention may comprise fructose and fructose oxidase.

Compositions of the invention may thus comprise only one sugar or sugar derivative which is the solute and the substrate, and one enzyme for converting the substrate and generating hydrogen peroxide.

In some embodiments, the solute with the solubility of at least 100 g/100 g water at 20° C. and 1 atm, at least 200 g/100 g water at 20° C. and 1 atm or at least 300 g/100 g water at 20° C. and 1 atm, may be distinct from the purified substrate. For example, a composition of the invention may comprise glucose, glucose oxidase and fructose.

In preferred embodiments, the purified substrate is a sugar or sugar derivative (e.g. glucose) and the solute is a sugar or sugar derivative (e.g. fructose).

Preferably, the composition comprises at least two sugars or sugar derivatives (e.g. including glucose and fructose). The composition may comprise a maximum of two sugars or sugar derivatives (e.g. only glucose and fructose).

Compositions of the invention may comprise at least 5% by weight of sugars and/or sugar derivatives. Compositions of the invention may comprise at least 10% by weight of sugars and/or sugar derivatives. Compositions of the invention may comprise at least 25% by weight of sugars and/or sugar derivatives. Compositions of the invention may comprise at least 50% by weight of sugars and/or sugar derivatives. Compositions of the invention may comprise 95% by weight or less of sugars or sugar derivatives. Compositions of the invention may comprise at 75% by weight or less of sugars and/or sugar derivatives. For example, compositions of the invention may comprise 10% to 95% by weight sugars and/or sugar derivatives. Compositions of the invention may comprise 25% to 75% by weight sugars and/or sugar derivatives. Compositions of the invention may comprise 50 to 95% by weight sugars and/or sugar derivatives.

Compositions of the invention may comprise 5 to 50% by weight of substrate for the enzyme (e.g. glucose) or 5 to 50% by weight of the precursor substrate that can be converted to the substrate for the enzyme. For instance, compositions of the invention may comprise 5 to 25% by weight of substrate for the enzyme (e.g. glucose) or 5 to 25% by weight of the precursor substrate that can be converted to the substrate for the enzyme Compositions of the invention may comprise 5 to 75% by weight of solute (e.g. fructose). For instance, compositions of the invention may comprise 10 to 50% by weight of solute.

Compositions of the invention may comprise a buffer, or a component that may be capable of acting as act as a buffer in an aqueous solution. An example of a suitable buffer is a citric acid/NaOH buffer, such as a 50 mMol citric acid/NaOH buffer. Compositions of the invention may be buffered (or may be capable of being buffered in an aqueous solution) at a pH of 5 or less, e.g. 3 to 5 (such as about pH 4). Alternatively, compositions of the invention may be buffered (or may be capable of being buffered in an aqueous solution) at a pH greater than 5, e.g. 6 to 8 (such as about pH 7).

Compositions of the invention preferably comprise substantially no peroxidase, or are essentially free of peroxidase.

Compositions of the invention preferably comprise substantially no zinc oxide, or are essentially free of zinc oxide.

A composition of the invention may comprise at least one suitable antimicrobial or immunostimulatory component, excipient or adjuvant, or any other suitable component where it is desired to provide ability to generate antimicrobial activity. Compositions of the invention may not comprise an antibiotic.

Compositions of the invention may comprise a salt.

Compositions of the invention may comprise a blood clotting agent. For example, compositions of the invention may comprise a coagulation factor. Potential coagulation factors include fibrinogen or thrombin. Artificial blood clotting agents could be included in compositions of the invention. Examples of such agents include carriers, such as albumin carriers, to which fibrinogen-binding peptides are immobilised.

Compositions of the invention are preferably sterile. Compositions of the invention may be sterilised by any suitable means. Preferably compositions of the invention have been sterilised by irradiation. The Applicant has found that compositions can retain glucose oxidase activity (and, therefore, the ability to release hydrogen peroxide on dilution) following sterilisation by exposure to gamma radiation or electron beam radiation. A suitable level of gamma irradiation is 10-70 kGy, preferably 25-70 kGy, more preferably 35-70 kGy. Alternatively, compositions of the invention may be sterilised by electron beam irradiation. A suitable level or dose of irradiation (e.g. electron beam irradiation) may be 10-100 kGy, preferably 30-80 kGy, more preferably 50-80 kGy. The dose may be greater than 35 kGy. The dose may be less than 80 kGy, for example 75 kGy or less. In one embodiment, compositions of the invention may be sterilised by irradiation that is not gamma irradiation.

There is also provided according to the invention a method of sterilising a composition of the invention, which comprises exposing the composition to irradiation, preferably gamma irradiation or electron beam irradiation.

Since ozone has not been authorised by the US FDA for sterilisation of honey-based products for use in wound healing, compositions according to the invention preferably have not been sterilized by ozonation, and do not include ozone, or any components that have been subjected to sterilisation by ozonation. In particular, compositions according to the invention should not comprise ozonized honey or ozonated oil.

Preferred compositions for medical use according to the invention are sterile, single use compositions.

Sterilised compositions for use according to the invention that are stored away from exposure to light are expected to retain stability for at least six months. For example, such compositions may be packaged in high-density polyethylene/low-density polyethylene (HDPE/LDPE) tubes or in polyester-aluminium-polyethylene (PET/Al/PE) sachets.

A composition of the invention is preferably a medical grade or medical device grade composition. A composition of the invention may be a pharmaceutical grade composition.

A composition of the invention may be provided with a wound dressing material to form a wound dressing. For example, the wound dressing material may be impregnated with the composition or the composition may be immobilised to the wound dressing material. Suitable wound dressing materials include gauzes, bandages, tissues, films, gels, foams, hydrocolloids, alginates, polysaccharide pastes, granules or beads. The composition may be present together with a wound-dressing matrix, such as a collagen or collagen-glycosaminoglycan matrix. The dressing may be a tulle dressing. Compositions in combination with a dressing are preferably sterile, and may be sterilised using irradiation, e.g. gamma irradiation. The wound dressing material may be impregnated with the composition, or the composition may be immobilised on the dressing material, such as on a surface of the dressing material.

The invention may provide a kit comprising a wound dressing material and, separately, a composition of the invention.

A composition of the invention may be provided in a container. Preferably the container is designed such that moisture in the air is prevented from entering the container and being absorbed by the composition. For example, the container may be an airtight container. The container may comprise a dessicant, such as silica gel. The composition in the container is preferably sterile whilst in the container. The container may be opaque.

The container may be designed to enable the composition to be dispensed. For example, the container may define one or a plurality of holes or apertures. The holes or apertures may be covered or sealed prior to use, for example using a cap, such as an airtight cap. The cover or seal may be removable and replaceable. The one or plurality of holes or apertures may permit dispensing of the composition when the container is inverted and shaken by a user.

Alternatively, the container may be a powder spray, such as a pressurised powder spray.

As described above, the composition may form a gel when it is contacted with water or a water-containing fluid, such as an aqueous solution (e.g. a bodily fluid such as wound exudate). Consequently, according to the invention, there is provided a gel, preferably a hydrogel, comprising an enzyme that is able to convert a substrate to release hydrogen peroxide; a substrate for the enzyme; and a superabsorbent material.

According to the invention, there is provided a gel, preferably a hydrogel, comprising an enzyme that is able to convert a substrate to release hydrogen peroxide; a precursor-substrate that can be converted into a substrate for the enzyme; and a superabsorbent material.

The enzyme, substrate and precursor-substrate may have any of the characteristics as already described herein. For example, it is preferable that the enzyme is a purified enzyme, the substrate is a purified substrate and the precursor-substrate is a purified precursor-substrate.

It is envisaged that the gel could form in situ, such as at the site of the wound, following application of the composition of the invention (e.g. in powder form) to a wound site. However, it is also possible that the gel could be pre-formed before application to a patient. For example, a user may mix the composition with water to form the gel, and then the gel may be applied to a wound site. The gel may be used in conjunction with a wound dressing, such as a gauze, bandage, tissue, film, gel, foam, hydrocolloid, alginate, polysaccharide paste, granules or beads.

Gels of the invention may be more elastic than viscous. So, when viscoelasticity is tested at a specific frequency, say at a frequency from 1 to 10 Hz, the storage modulus may be higher than the loss modulus.

Increasing the amount of superabsorbent component in the composition (e.g. increasing the amount of superabsorbent polymer) may increase the stiffness of the resulting gel.

Compositions of the invention may be used to treat any microbial infection that can be treated by hydrogen peroxide. Examples include infection caused by gram positive bacteria, gram negative bacteria, acid-fast bacteria, viruses, yeasts, parasitic or pathogenic micro-organisms or fungi. For example, infections caused by the following micro-organisms may be treated: *Escherichia coli, Staphylococcus aureus, Pseudomonas aeruginosa, Candida albicans, Propionibacterium acnes, Staphylococcus aureus, Staphylococcus epidermidis, Staphylococcus* saprophytics, Beta haemolytic Streptococci Group A or B, *Campylobacter* coil, *Campylobacter jejuni*, Methicillin Resistant *Staphylococcus Aureus* (MRSA), Methicillin Sensitive *Staphylococcus Aureus* (MSSA), *Botrytis cinerea, Mycobacterium tuberculosis, Cryptosporidium, Plasmodium, Streptococcus pyogenes, streptococcus zooepidemicus* and *Toxoplasma*.

There is further provided according to the invention a composition of the invention for use in the prevention or treatment of a microbial infection, for example a microbial infection that comprises a biofilm, or a microbe that is capable of forming a biofilm. So, there may be provided a compositions of the invention for use in the prevention or treatment of a microbial infection that comprises a biofilm or a microbe that is capable of forming a biofilm. The biofilm may comprise bacteria, fungi and/or viruses.

There is also provided according to the invention use of a composition of the invention in the manufacture of a medicament for the prevention or treatment of a microbial infection, for example a microbial infection that comprises a biofilm, or a microbe that is capable of forming a biofilm.

The invention also provides a method of preventing or treating a microbial infection, for example a microbial infection that comprises a biofilm, or a microbe that is capable of forming a biofilm, wherein the method comprises administering an effective amount of a composition of the invention to a site of the infection.

According to the invention there is also provided use of a composition or solution of the invention to prevent or inhibit microbial growth.

There is also provided according to the invention a composition of the invention for use as a medicament.

Compositions of the invention may be used to treat animals. Compositions of the invention may be used to treat humans.

There is further provided according to the invention a composition of the invention for the prevention, treatment, or amelioration of a microbial infection.

The invention also provides use of a composition or solution of the invention in the manufacture of a medicament for the prevention, treatment, or amelioration of a microbial infection.

There is further provided according to the invention a method of preventing, treating, or ameliorating a microbial infection, which comprises administering a composition or solution of the invention to a subject in need of such prevention, treatment or amelioration. The subject may be a human or animal subject. Compositions of the invention may be topically administered.

Compositions of the invention may be for administration to surgical wounds.

Compositions of the invention with a high osmolarity (suitably having a water activity ($a_w$) in the range similar to honey, i.e. 0.47-0.7) are believed to facilitate the debridement of wounds by the autolytic action of tissue proteases. They may create a moist wound environment by drawing out lymph fluid from the wound tissues through their strong osmotic action. This provides a constant supply of proteases at the interface of the wound bed and the overlying necrotic tissue. This action also washes the surface of the wound bed from beneath. The debriding action may also contribute to the lowering of a wound's bacterial load by removal of dead tissue. Dead tissue is well known to provide an excellent medium for bacterial growth and increase the risk of infections if left in the wound. The amount of 'free' water in honey is measured as the water activity ($a_w$). Compositions of the invention may have a water activity of 0.7 or lower.

According to a preferred aspect of the invention, a composition of the invention may be used in a method of wound care, including the treatment of a wound, or the treatment or management of wound sepsis.

The wound may be an acute wound, chronic wound, surgical wound (for example, a Caesarean wound), chronic burn, or an acute burn. A composition of the invention may be used in the prophylactic prevention of wound sepsis. If a storage-stable composition of the invention is used, it will be appreciated that this may be diluted by liquid present at the wound site, which thereby leads to the release of hydrogen peroxide by the diluted composition.

According to the invention there is provided a method of treating a wound, which comprises administering a composition of the invention to the wound.

There is also provided according to the invention a composition of the invention for treatment of a wound.

Compositions of the invention may be used to treat wounds that are critically colonized. The term "critically colonized" is often used to refer to a wound that has reached a critical point at which bacteria begin to negatively affect the wound and begin to elicit signs of their presence. A critically colonized wound may indicate the presence of a biofilm. A bacterial load of greater than $10^5$ organisms/gram of tissue is often accepted as impeding wound healing (Siddiqui A R, Bernstein J M (2010) Chronic wound infection: Facts and controversies. Clinics in Dermatology 28: 519-26; Edmonds, M., & Foster, A. (2004). The use of antibiotics in the diabetic foot. Am J Surg, 187(5A), 25S-28S. Consequently, compositions of the invention may be used to treat wounds that have a bacterial load of greater than $10^5$ organisms/gram of tissue.

There is further provided according to the invention use of a composition of the invention in the manufacture of a medicament for treatment of a wound.

There is also provided according to the invention a method of treating inflammation, which comprises administering a composition of the invention to a site of inflammation.

There is also provided according to the invention a composition of the invention for treatment of inflammation.

There is further provided according to the invention use of a composition of the invention in the manufacture of a medicament for treatment of inflammation.

There is also provided according to the invention a method of stimulating tissue growth, which comprises administering a composition of the invention to a site in need of such stimulation.

There is also provided according to the invention a composition of the invention for stimulating tissue growth.

There is further provided according to the invention use of a composition of the invention in the manufacture of a medicament for stimulating tissue growth.

There is also provided according to the invention a method of debriding a wound, which comprises administering a composition of the invention to a wound in need of debridement.

There is also provided according to the invention a composition of the invention for debriding a wound.

There is further provided according to the invention use of a composition of the invention in the manufacture of a medicament for debriding a wound.

There is also provided according to the invention a method of deodorising a wound, which comprises administering a composition of the invention to a wound in need of deodorising.

There is also provided according to the invention a composition of the invention for deodorising a wound.

There is further provided according to the invention use of a composition of the invention in the manufacture of a medicament for deodorising a wound.

For wound healing applications, compositions of the invention may be administered at an appropriate frequency determined by the healthcare provider. Suitably compositions of the invention may be administered at least every several days, for example every week, but preferably every day or every other day.

The amount of a composition of the invention administered will depend on many factors, such as the strength of the antimicrobial properties of the composition, and other wound healing properties of the composition, on the size of the wound, and on the age and condition of the subject to be treated. However, for many applications it is expected that administration of 2-100 g, or 5-100 g of a composition of the invention will be suitable, preferably 10-50 g.

According to the invention, there are also provided methods for making compositions of the invention.

According to the invention, there is provided a method for making a composition of the invention, comprising contacting an enzyme that is able to convert a substrate to release hydrogen peroxide, with a substrate for the enzyme and a superabsorbent component.

The enzyme and substrate may already be mixed, prior to contacting with the superabsorbent component. For example, the enzyme and substrate may be present in a liquid honey-based composition, such as SurgihoneyRO™, which is a honey containing added glucose oxidase, the honey having been pasteurised and sterilised by exposure to irradiation.

Alternatively, enzyme and substrate may be in a synthetic honey composition. The synthetic honey may comprise a purified enzyme, a purified substrate (or purified precursor-substrate) and a purified solute, as disclosed in any form herein. For instance, the solute may be in the form of a sugar or sugar derivative having a solubility of at least 100 g/100 g water at 20° C. and 1 atm. In a particularly preferred embodiment, the solute is fructose. So, in one embodiment, the method may involve using a composition comprising glucose, glucose oxidase and fructose. The solute may be at least 60% by dry weight of the composition. The substrate or precursor-substrate may be at least at 30% by dry weight of the composition. The combined dry weight of the substrate and the solute, or the precursor-substrate and the solute, may be at least 90%, preferably at least 95% of the composition. The total amount of sugar or sugar derivative in the composition may be at least 90%, by dry weight, preferably at least 95%, by dry weight.

The composition for use in the method may comprise 20% by weight, or less, of water. The composition for use in the method may comprise at least 10%, preferably at least 15% by weight of water.

The composition for use in the method may comprise at least 70%, more preferably at least 75%, by weight, or even more preferably at least 80%, by weight, of the substrate and solute combined, or the precursor-substrate and solute combined.

The composition for use in the method may be characterised in that the total amount of sugar or sugar derivative is at least 70%, more preferably at least 75%, by weight, or even more preferably at least 80%, by weight.

The composition for use in the method may be a liquid. If the composition for use in the method is a liquid, the method may comprise freeze-drying or lyophilising the composition to form a powder. If the method involves freeze-drying or lyophilising, a freeze-drying protective agent may be added to the composition. Suitable freeze-drying protective agents have been described herein.

If a composition of the invention has been formed by freeze-drying, it may comprise distinct powder particles of which each particle contains both the enzyme and the substrate (or precursor-substrate). If a composition of the invention has been formed by mixing powders rather than by freeze-drying, it may comprise distinct particles containing only enzyme and only substrate (or precursor-substrate).

In some embodiments, freezing and milling may take place before freeze-drying. This may allow more efficient drying.

Once the composition has been freeze-dried, it may then be contacted with a superabsorbent component, as described herein.

Alternatively, compositions of the invention may be formed by mixing powder forms of the enzyme, the substrate (or precursor-substrate) and the superabsorbent polymer.

Preferred embodiments of the invention are now described, by way of example only, with reference to the accompanying drawings in which.

Figure 8:
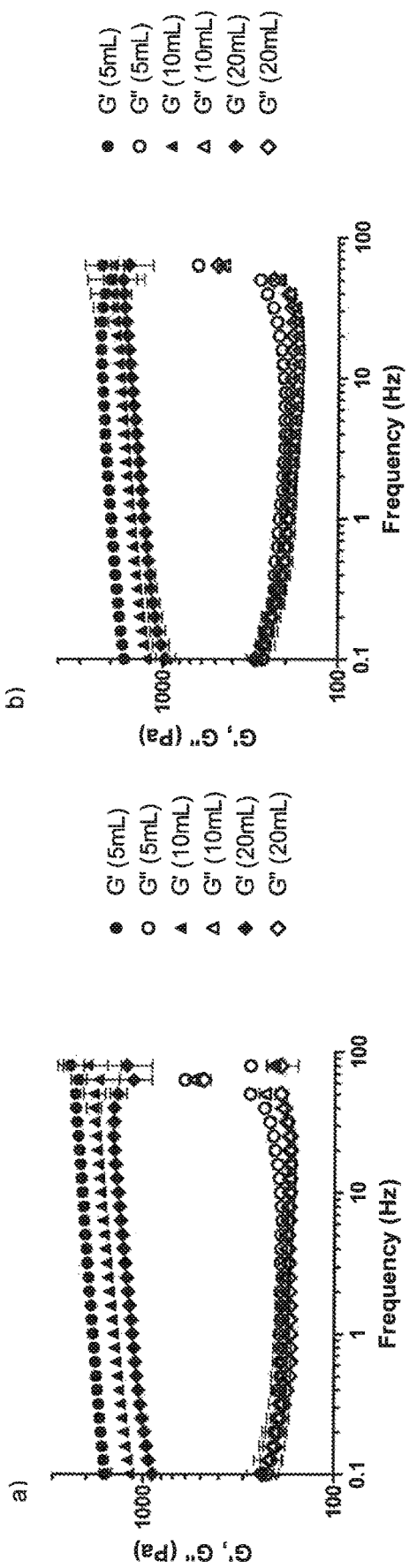
Figure 9:
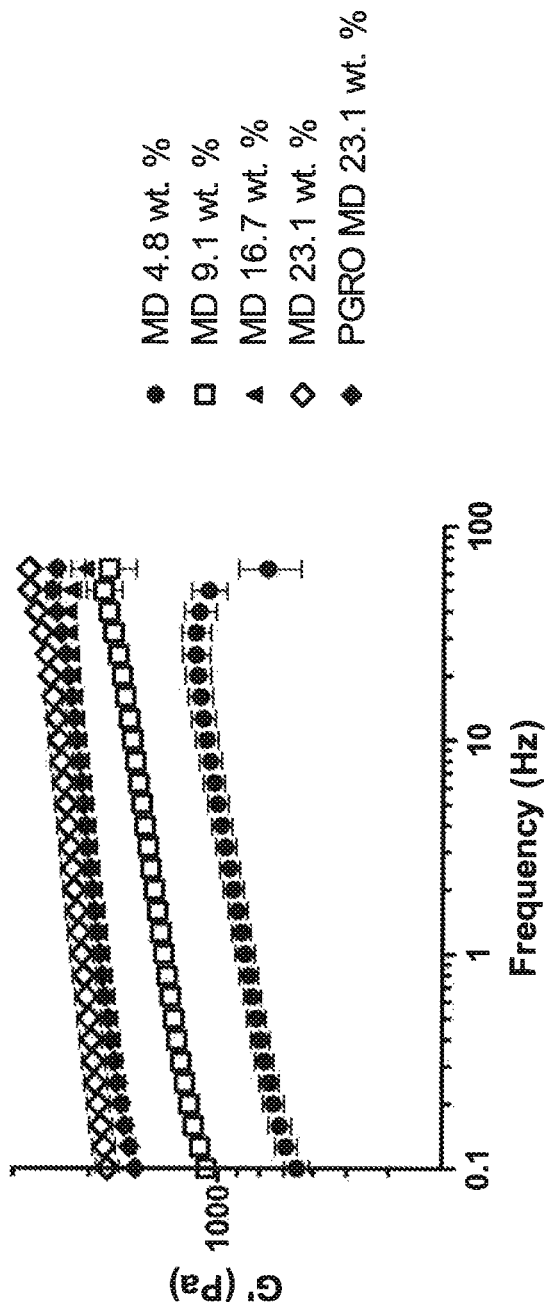
Figure 10:
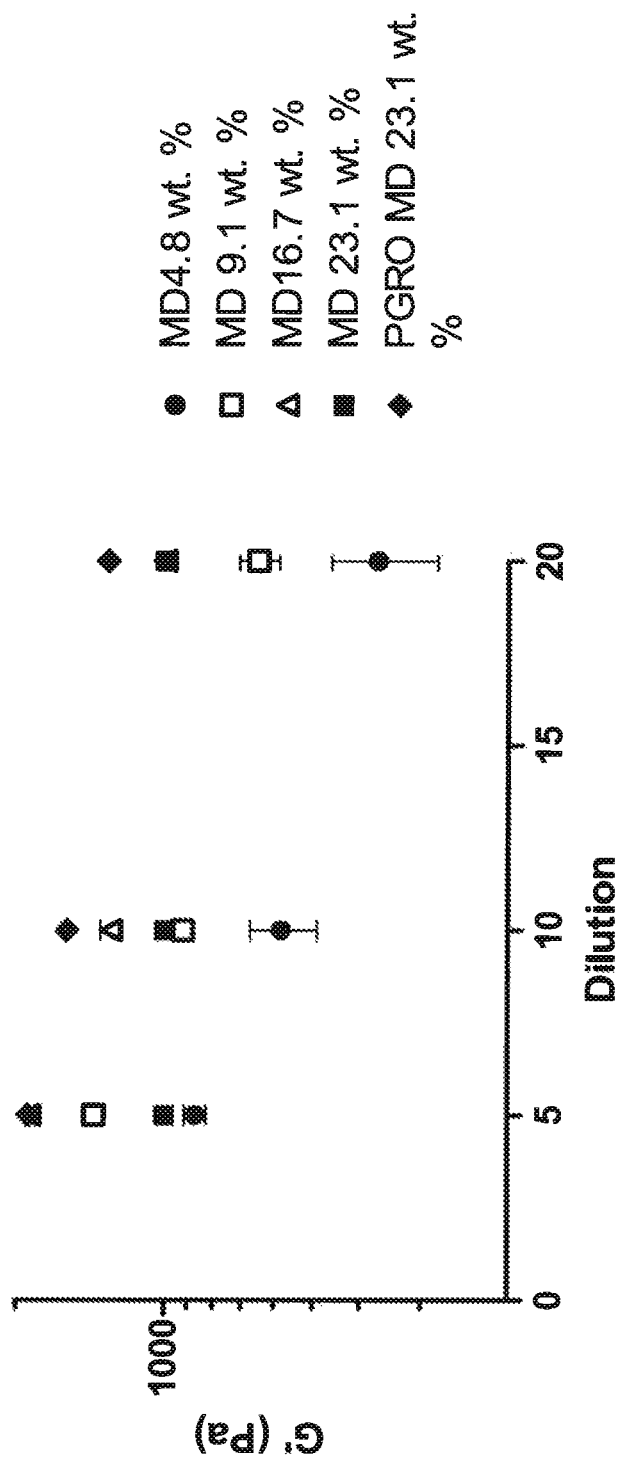
Figure 11:
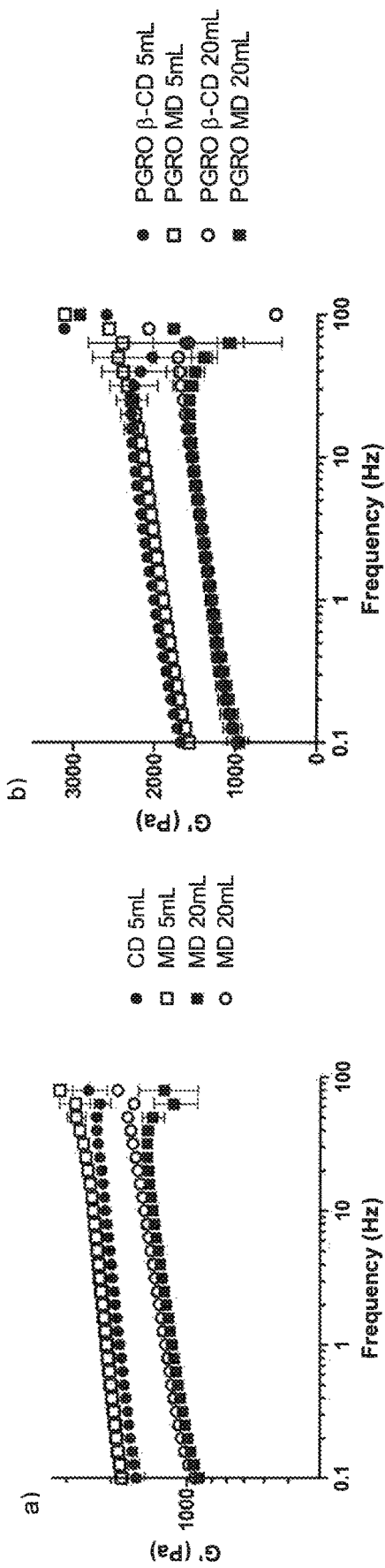
Figure 12:
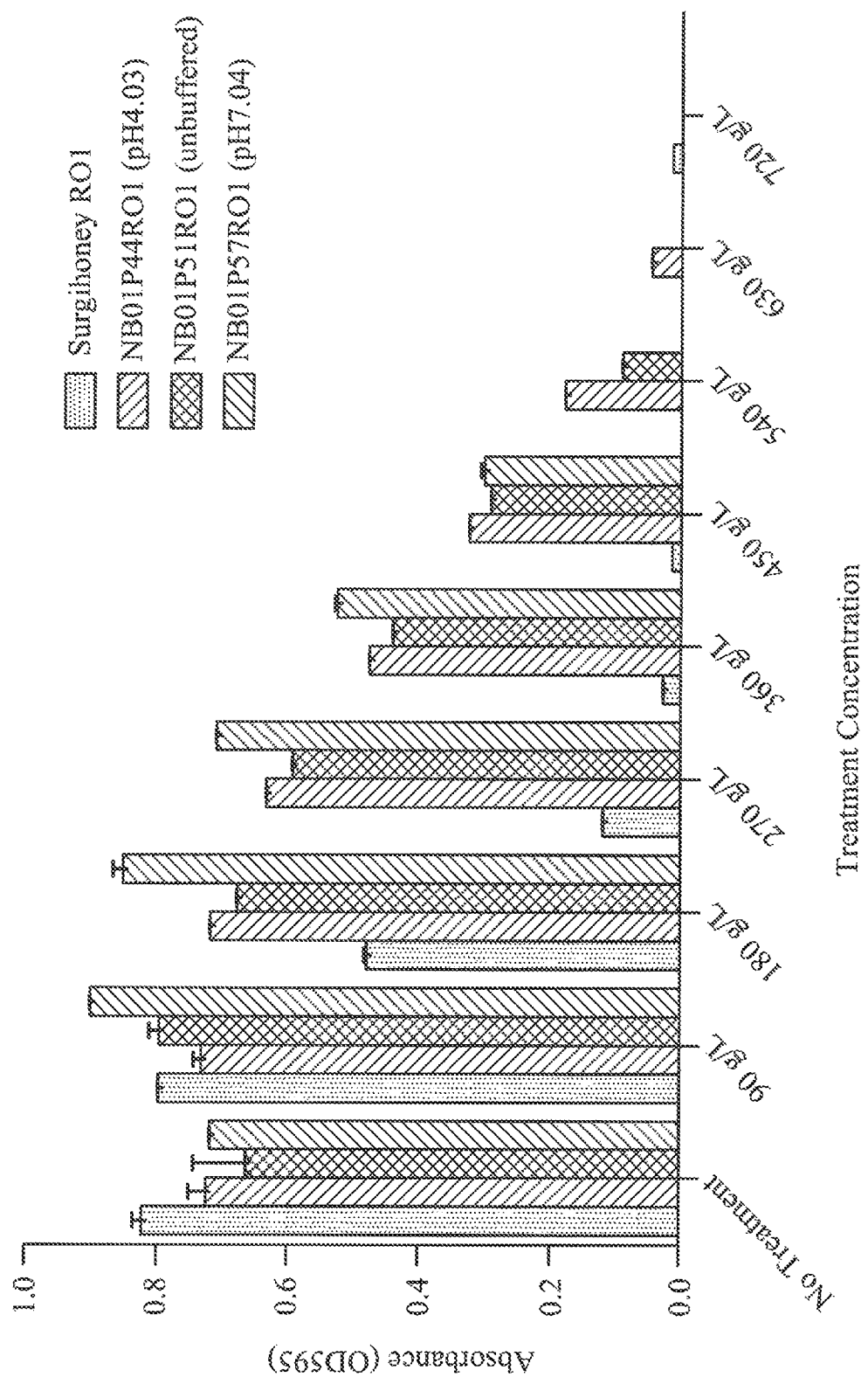
Figure 17:
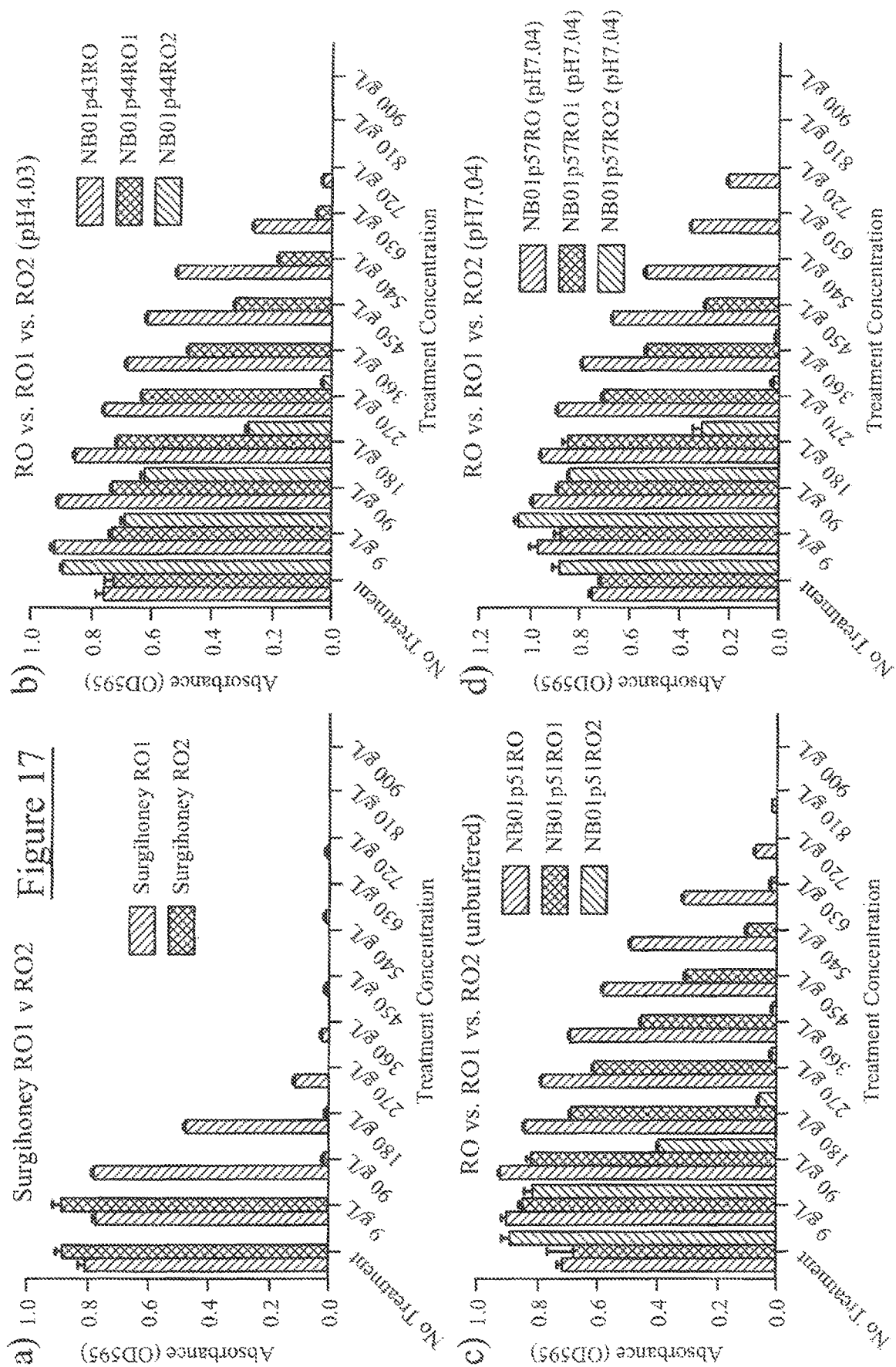

FIG. 8 the effect of dilution upon the physical properties of examples of gels of the invention;

FIG. 9 shows the effect of increasing the amount of cross-linked sodium polyacrylate on viscoelastic properties of examples of gels of the invention;

FIG. 10 shows the effect of dilution at a fixed frequency (1 Hz) upon the storage modulus of examples of gels of the invention;

FIG. 11 shows a comparison of storage modulus values at different dilutions between different examples of gels of the invention;

FIG. 12 is a graph showing the effect of compositions suitable for use in forming examples of superabsorbent powders of the invention comprising glucose, glucose oxidase and fructose (SyntheticRO) on the growth of planktonic MRSA, compared to Surgihoney™, at various concentrations;

FIG. 13 is a graph showing the effect of sterile and non-sterile compositions suitable for use in forming examples of superabsorbent powders of the invention, comprising glucose, glucose oxidase and fructose (SyntheticRO) (buffered at pH 4.03) on the growth of planktonic MRSA, at various concentrations;

FIG. 14 is a graph showing the effect of sterile and non-sterile compositions suitable for use in forming examples of superabsorbent powders of the invention, comprising glucose, glucose oxidase and fructose (SyntheticRO) (unbuffered) on the growth of planktonic MRSA, at various concentrations;

FIG. 15 is a graph showing the effect of sterile and non-sterile compositions suitable for use in forming examples of superabsorbent powders of the invention, comprising glucose, glucose oxidase and fructose (SyntheticRO) (buffered at pH 7.04) on the growth of planktonic MRSA, at various concentrations;

FIG. 16 is a table showing the effect of sterile and non-sterile compositions suitable for use in forming examples of superabsorbent powders of the invention comprising glucose, glucose oxidase and fructose, on the MIC and MBC of planktonic MRSA, at various concentrations;

FIG. 17 shows the effect of compositions suitable for use in forming examples of superabsorbent powders of the invention, comprising glucose, glucose oxidase and fructose (SyntheticRO) on the growth of planktonic MRSA, compared to SurgihoneyRO, at various concentrations;

FIG. 18 shows the effect of SyntheticRO on the MIC and MBC of planktonic MRSA, compared to SurgihoneyRO, at various concentrations;

SPECIFIC EXAMPLES

Example 1—Synthesis of Superabsorbent Powder

SurgihoneyRO (Sachet) or SyntheticRO (a mixture of purified glucose oxidase, purified glucose and purified fructose; see example 5) and either methylated β-Cyclodextrin (CycloLab R&D, UK) or Maltodextrin (Sigma Aldrich, UK) were first weighed out in equal proportions (50:50 ratio).

The desired amount (0.5, 1, 2 or 3 g) of cross-linked sodium polyacrylate (Sigma Aldrich, UK) was also weighed out.

All three components were then mixed together until a homogenous formulation was achieved. This formulation was then placed inside a freezer mill tube and submerged in liquid nitrogen for approximately 1 minute. The freezer mill tube was then placed in the freezer mill (SPEX SamplePrep). The freezer mill was run at a rate of 30 cycles per second for a total time of 3 minutes.

For compositions containing SurgihoneyRO, it was found that milling the mixture first allowed for a more complete drying process.

The samples were then transferred into the freeze drying chamber (Frozen in Time). The freeze drier cold trap was set to −55° C. and was at a pressure of $4.0 \times 10^{-4}$ mbar. The sample was freeze dried for a total of 48 hours.

The samples were removed and sieved using 1000 μm and 500 μm gratings. Any powder that remained in the sieves was crushed using a pestle and mortar and ran through the sieves again. The powder was then sealed in a pot containing silica gel beads which act as a desiccant.

Example 2—Formation of Gels

To demonstrate formation of gels, water was added to a powder containing 40:60 SurgihoneyRO™ to cyclodextrin composition containing 3 wt % sodium polyacrylate.

Figure 1:
FIG. 1 shows a photograph of a superabsorbent powder according to an embodiment of the invention, prior to addition of water.

FIG. 1 shows 1 g of the powder prior to addition of water, in a weighing boat.

Figure 2:
FIG. 2 shows the resulting gel following addition of 15 ml of water to a superabsorbent powder according to an embodiment of the invention, with a hydrogen peroxide test strip indicating hydrogen peroxide production.
Figure 3:
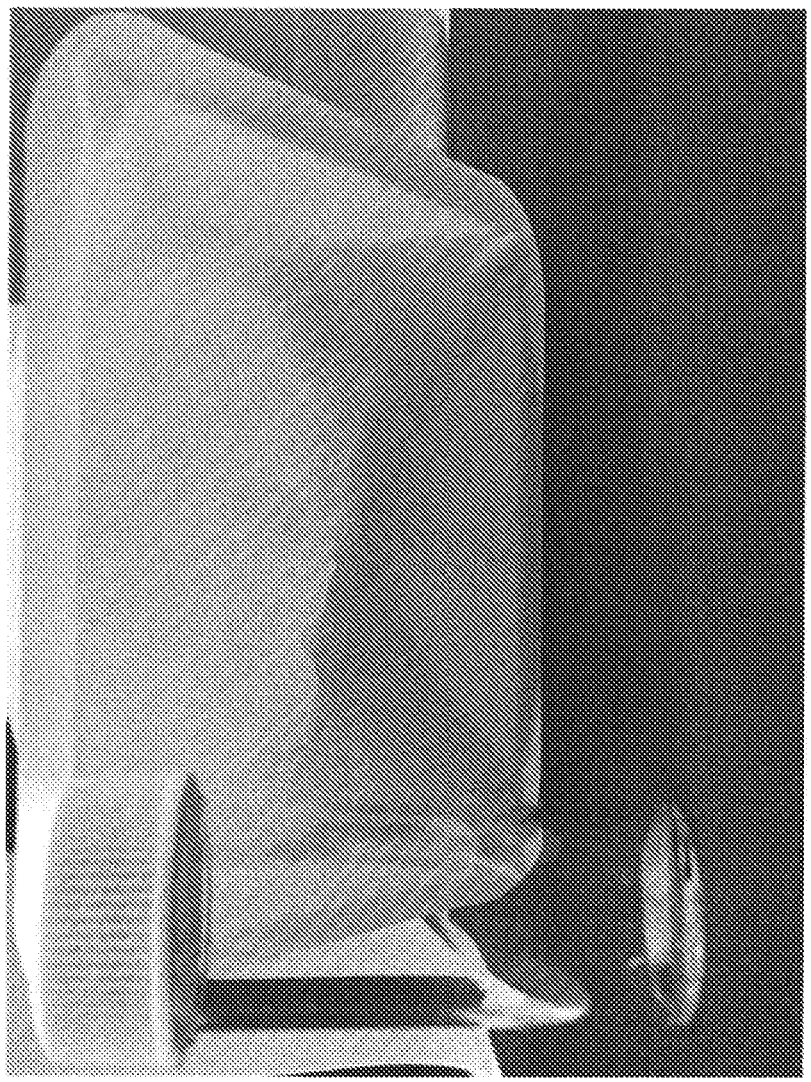
FIG. 3 shows the gel of FIG. 2, in an inverted orientation.

FIG. 2 shows the resulting gel following addition of 15 ml of water. It also shows a hydrogen peroxide test strip indicating the production of hydrogen peroxide by the gel. FIG. 3 shows the same gel, but in an inverted orientation. This demonstrates how the gel may readily adhere to a surface.

Figure 4:
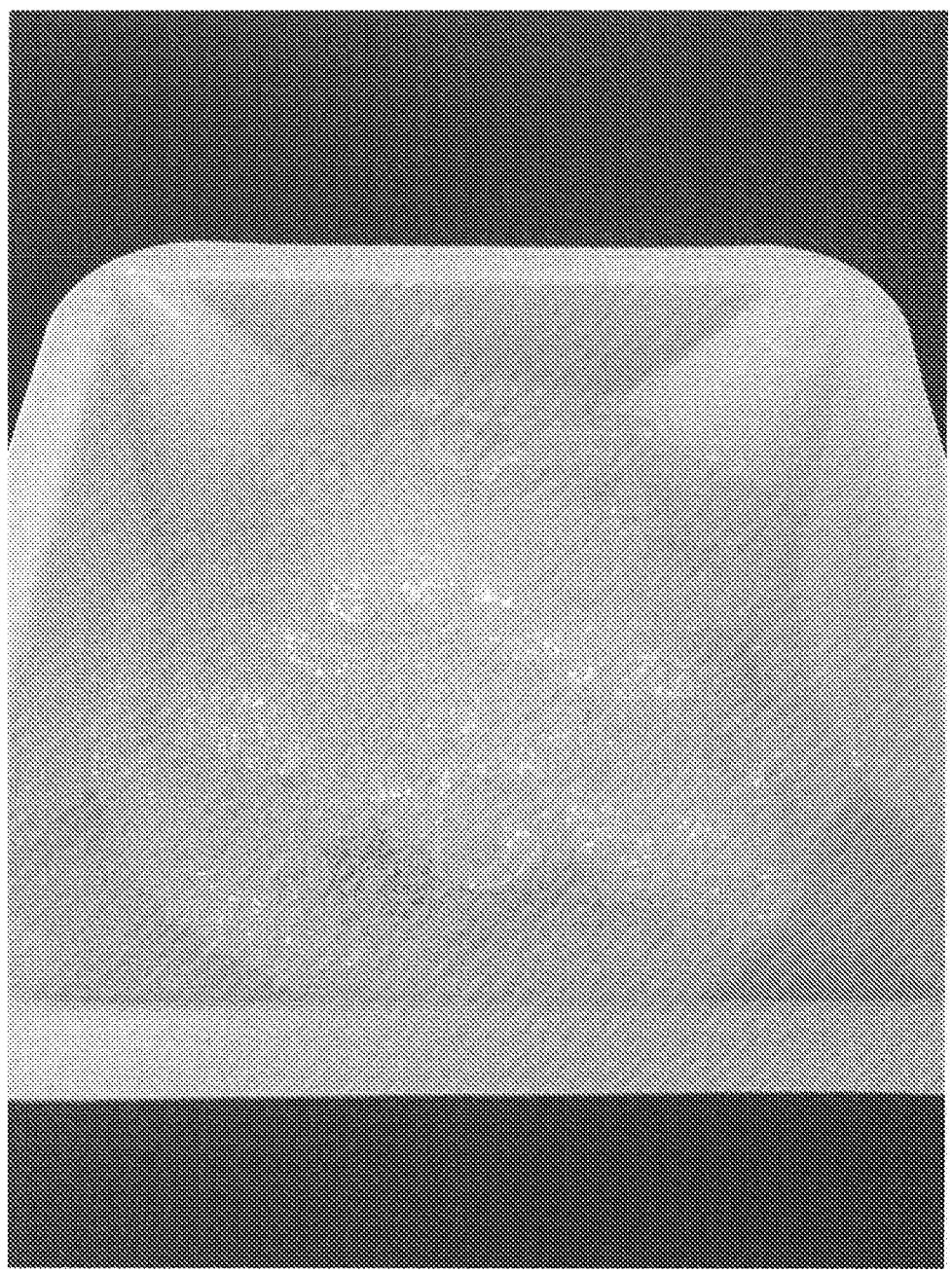
FIG. 4 shows a gel following addition of 30 ml of water to a superabsorbent powder according to an embodiment of the invention.
Figure 5:
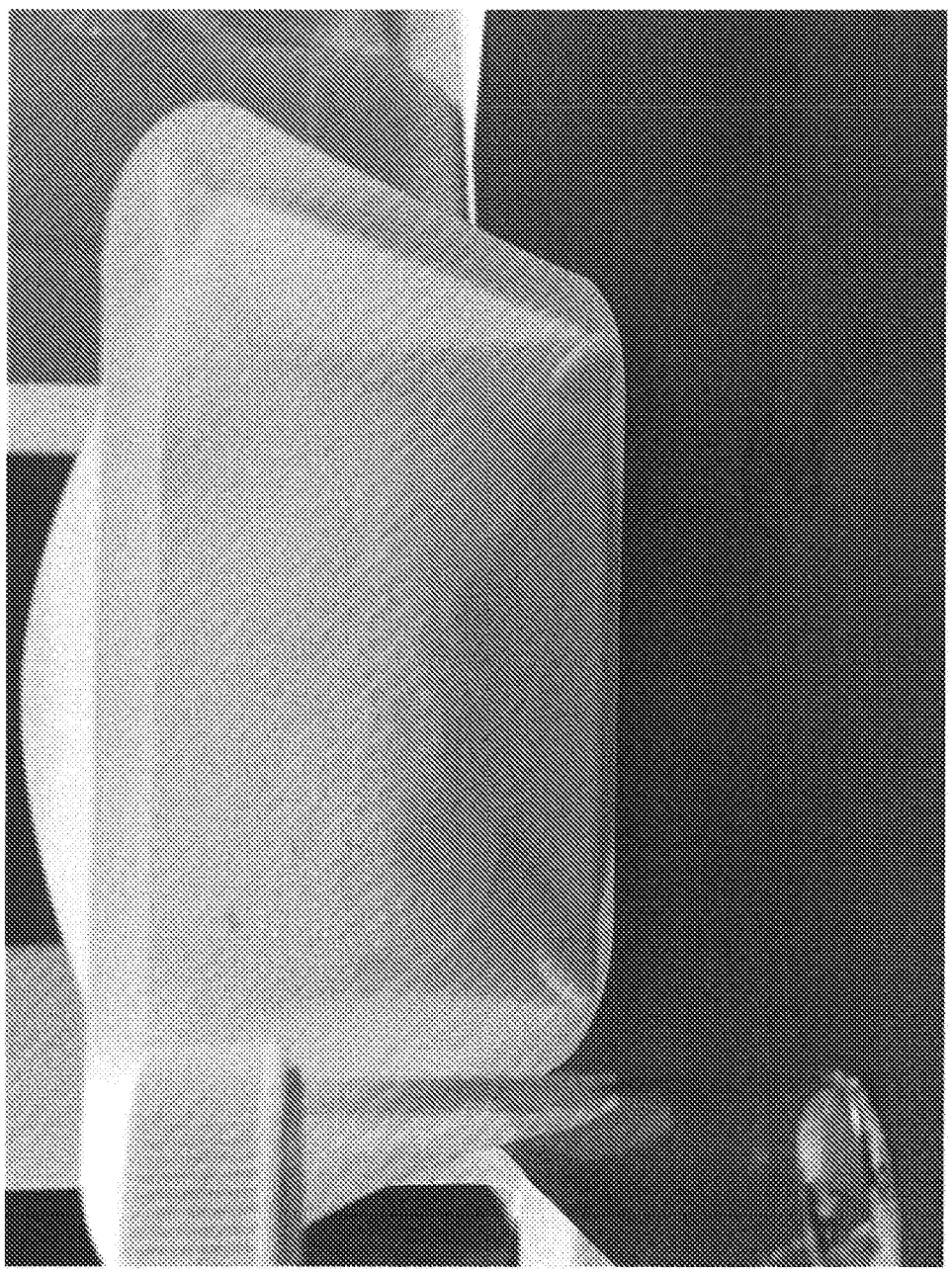
FIG. 5 shows the gel of FIG. 4 in an inverted orientation.

FIG. 4 shows the gel following addition of 30 ml of water, and FIG. 5 shows the same gel in an inverted orientation.

Example 3—Particle Size Analysis

An instrument called QICPIC (Sympatec, UK) was employed, which uses of dynamic image analysis to size particles. High speed image analysis used a pulsed light source with illumination times of less than 1 nanosecond. The particles are optically frozen while a high-resolution, high-speed camera captures the particle projections. Algorithms built into the instrument software evaluate the particles giving statistically relevant results. The following parameters were used in order to determine particle size:

Calculation mode: EQPC—this mode is used to calculate the diameter of a circle that has the same area as the projection area of the particle.

Trigger condition: start 0s, valid 300 s

Dispersing method: 2 mm 25% 4 mm
Frame rate: 100 fps
Height of fall: 40.00 cm
Feeder: Vibrate
Feed rate: 25.00%
Gap height: 2.00 mm The amount of superabsorbent polymer in the compositions and the type of freeze-drying protective agent was varied in order to establish the impact of varying these parameters on the properties of the compositions.

The following compositions were tested, and their peak particle distributions and sphericities were established.

A superabsorbent reactive oxygen powder containing 47.6 wt. % methylated β-Cyclodextrin, 47.6 wt. % SurgihoneyRO and 4.8 wt. % cross-linked sodium polyacrylate.

This composition contains a peak particle size distribution at 204.5 μm and a peak sphericity distribution at 0.9.

A superabsorbent reactive oxygen powder containing 45.5 wt. % methylated β-Cyclodextrin, 45.5 wt. % SurgihoneyRO and 9.1 wt. % cross-linked sodium polyacrylate.

This composition contains a peak particle size distribution at 204.5 μm and a peak sphericity distribution at 0.9.

A superabsorbent reactive oxygen powder containing 41.7 wt. % methylated β-Cyclodextrin, 41.7 wt. % SurgihoneyRO and 16.7 wt. % cross-linked sodium polyacrylate.

This composition contains a peak particle size distribution at 186.4 μm and a peak sphericity distribution at 0.9.

A superabsorbent reactive oxygen powder containing 38.5 wt. % methylated β-Cyclodextrin, 38.5 wt. % SurgihoneyRO and 23.1 wt. % cross-linked sodium polyacrylate.

This composition contains a peak particle size distribution at 204.5 μm and a peak sphericity distribution at 0.9.

A superabsorbent reactive oxygen powder containing 38.5% methylated β-Cyclodextrin, 38.5% wt. % SyntheticRO and 23.1 wt. % cross-linked sodium polyacrylate This composition contains a peak particle size distribution at 540.5 μm and a peak sphericity distribution at 0.82.

A superabsorbent reactive oxygen powder containing 47.6 wt. % maltodextrin, 47.6 wt. % SurgihoneyRO and 4.8 wt. % cross-linked sodium polyacrylate.

This composition contains a peak particle size distribution at 405.7 μm and a peak sphericity distribution at 0.85.

A superabsorbent reactive oxygen powder containing 45.5 wt. % maltodextrin, 45.5 wt. % SurgihoneyRO and 9.1 wt. % cross-linked sodium polyacrylate.

This composition contains a binomial distribution with peak particle size distributions at 445.0 μm and 2107.4 μm, a peak sphericity distribution at 0.85.

A superabsorbent reactive oxygen powder containing 41.7 wt. % maltodextrin, 41.7 wt. % SurgihoneyRO and 16.7 wt. % cross-linked sodium polyacrylate, This composition contains a peak particle size distribution at 445.0 μm a peak sphericity distribution at 0.85.

A superabsorbent reactive oxygen powder containing 38.5 wt,% maltodextrin, 38.5 wt. % SurgihoneyRO and 23.1 wt. % cross-linked sodium polyacrylate.

This composition contains a binomial distribution with peak particle size distributions at 445.0 μm and 2107.4 μm a peak sphericity distribution at 0.85.

A superabsorbent reactive oxygen powder containing 38.5 wt. % maltodextrin, 38.5 wt. % SyntheticRO and 23.1 wt. % cross-linked sodium polyacrylate.

The composition contains a polymodal distribution with peak particle size distributions at 540.5 μm, 968.4 μm and 1428.5 μm; and two peak sphericity distribution at 0.45 and 0.85.

Figure 6:
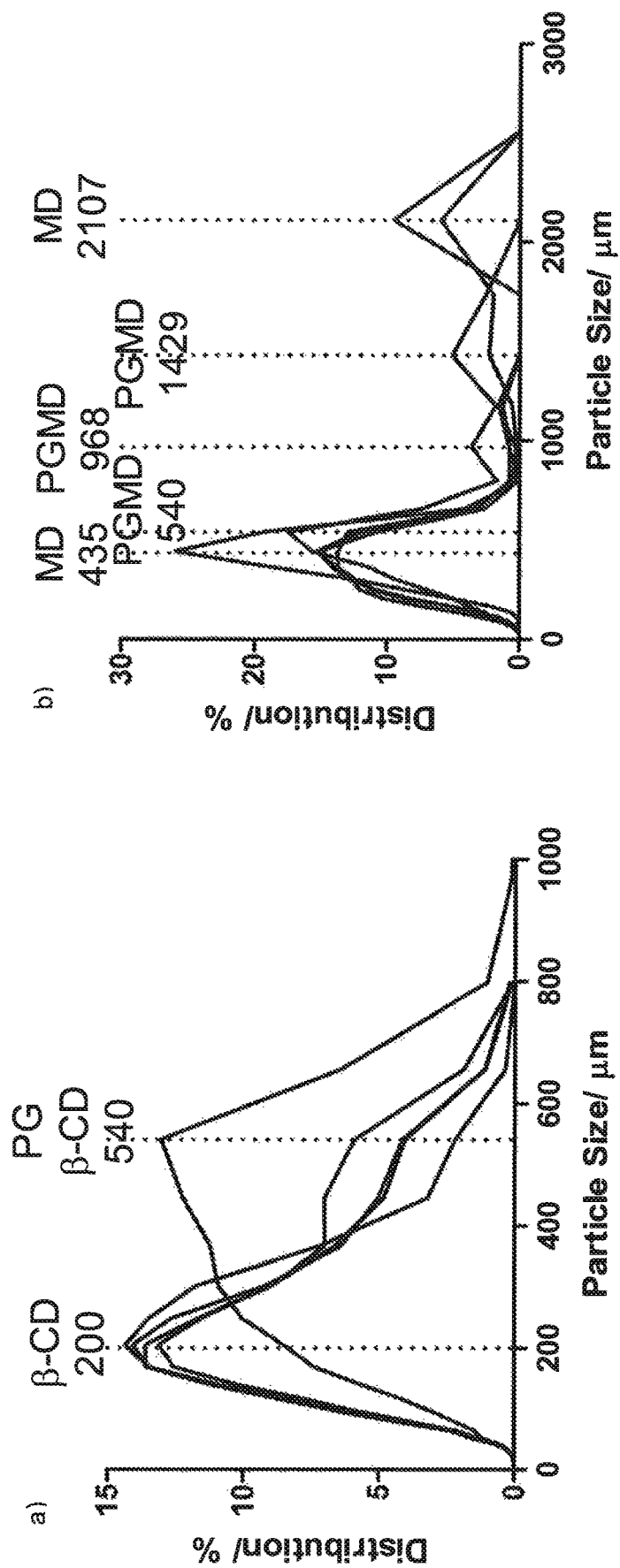
FIG. 6 shows the particle size distributions of examples of superabsorbent powder compositions of the invention.
Figure 7:
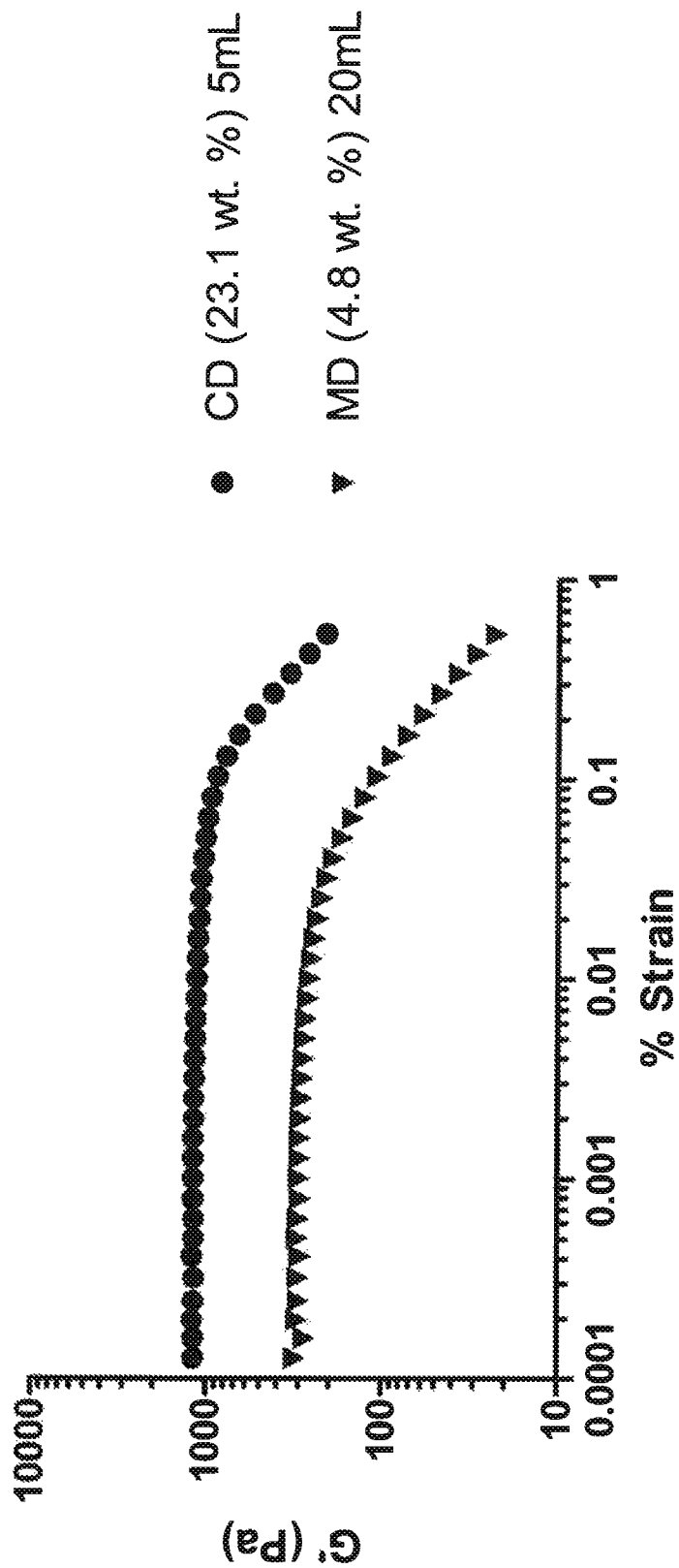
FIG. 7 shows a % strain sweep depicting the LVR for both extremes of current formulations including formulations which include maltodextrin and methylated β-Cyclodextrin.

FIG. 6 *a*) illustrates the particle size distributions of each composition containing β-cyclodextrin sodium polyacrylate and SurgihoneyRO/SyntheticRO. FIG. 6 *b*) illustrates the particle size distributions of each composition containing maltodextrin, sodium polyacrylate and SurgihoneyRO/SyntheticRO.

The results obtained suggest the following:

Increasing the wt % of cross-linked sodium polyacrylate may not affect particle size.

Compositions containing methylated β-cyclodextrin may have a smaller average particle size than those that contain maltodextrin.

Formulations that contain methylated β-cyclodextrin may produce more spherical particles.

Formulations containing Maltodextrin appear to aggregate or agglomerate to form larger particles post-sieving.

Example 4—Gel Rheology Analysis

Firstly the linear viscoelastic region (LVR) was determined for all of the tested powder gels. The LVR is determined so that the material behaves linearly and an out of phase sinusoidal shear stress response is produced. This was achieved by conducting a strain sweep on a Rheometer (TA Instruments, UK) using a 40 mm steel sand blasted plate geometry in parallel to another sand blasted steel plate.

FIG. 7 shows a % strain sweep depicting the LVR for both extremes of tested formulations including formulations which include maltodextrin (MD) and methylated β-Cyclodextrin (CD).

The strain sweep was conducted under the following conditions:

% strain range was set logarithmically from 0.01 to 50.0 with 10 points measured per decade.

Temperature set to 34° C. relevant to the final topical application with an equilibration time of 2 minutes.

The frequency was kept constant at 1 Hz

Geometry gap was set at 1000 μm

The strain sweep identified a % strain that fell into the LVR for all of the samples; this was found to be 0.5% strain.

Frequency sweeps were then carried out at this % strain and the following conditions:

Frequency range was set logarithmically from 0.1 and 100 Hz with 10 points measured per decade.

Temperature set to 34° C. relevant to the final topical application with an equilibration time of 2 minutes.

The same compositions as those in Example 3 were used to form gels by adding varying amounts of water (5 ml, 10 ml or 20 ml).

FIG. 8 *a*) shows the effect of dilution upon the physical properties of the gel formed from a composition containing 38.5 wt. % methylated β-cyclodextrin, 38.5 wt. % SurgihoneyRO and 23.1 wt. % cross-linked sodium polyacrylate, at a range of frequencies. FIG. 8 *b*) shows the same composition but with syntheticRO, rather than SurgihoneyRO.

The results indicate how shows how the gels formed may be more elastic than viscous (higher G' (storage modulus) than G" (loss modulus)), over the range of frequencies; and how there may be a low frequency dependency. Similar effects were observed for the other compositions.

FIG. 9 shows the effect of increasing the amount of cross-linked sodium polyacrylate in maltodextrin: SurgihoneyRO/SyntheticRO compositions containing 4.8 wt. %, 9.1 wt. %, 16.7 wt. % and 23.1 wt. % upon the storage modulus (G'). The gels were formed by adding 5 ml of distilled water. FIG. 9 shows how an increase in cross-linked sodium polyacrylate may increase the stiffness of the gel that is formed. Similar effects were observed for the other compositions.

FIG. 10 shows the effect of dilution at a fixed frequency (1 Hz) upon the storage modulus of the gel containing varying amounts of cross-linked sodium polyacrylate in maltodextrin: SurgihoneyRO/SyntheticRO formulations.

FIG. 11 a) shows a comparison of storage modulus values at different dilutions between gels formed from compositions containing maltodextrin: SurgihoneyRO and compositions containing methylated β-cyclodextrin: SurgihoneyRO, the compositions containing 16.7 wt. % cross-linked sodium polyacrylate. FIG. 11 b) shows results from the same formulations, but which contain SyntheticRO rather than SurgihoneyRO.

The results obtained suggest the following:
An increase in cross-linked sodium polyacrylate may increase the stiffness of the gel;
There is a low frequency dependency;
Samples may be more elastic than viscous;
Gels containing SyntheticRO may have a higher G' and G" than those which contain SurgihoneyRO;
There may be no significant difference between the rheology of the formulations that contain maltodextrin or cyclodextrin;
Cyclodextrin-based formulations may dissolve more readily upon application to water than those which contain maltodextrin.

Example 5—Synthetic Honey Compositions (Also Known as SyntheticRO)

Samples with batch number "RO" contain no glucose oxidase.
Samples with batch number "RO1" contain 50 ppm glucose oxidase.
Samples with batch number "RO2" contain 1000 ppm glucose oxidase.
A. pH 4.03 Buffered Samples
A1. Batch no NB01p43RO
Non sterile

| Material | Weight fraction |
|---|---|
| Fructose | 52.0% |
| Glucose | 31.0% |
| 50 mMol Citric acid/NaOH buffer pH 4.03 | 17.0% |

Description
Non sterile base buffered saccharide solution.
A2. Batch no NB01p43RO
Sterile

| Material | Weight fraction |
|---|---|
| Fructose | 52.0% |
| Glucose | 31.0% |
| 50 mMol Citric acid/NaOH buffer pH 4.03 | 17.0% |

Description Sterile base buffered saccharide solution
A3. Batch no NB01p44RO1
Non sterile

| Material | Weight fraction |
|---|---|
| Fructose | 52.0% |
| Glucose | 31.0% |
| 50 mMol Citric acid/NaOH buffer pH 4.03 | 17.0% |

Description
Non sterile base buffered RO1 saccharide solution.
A4. Batch no NB01p44RO1
Sterile

| Material | Weight fraction |
|---|---|
| Fructose | 52.0% |
| Glucose | 31.0% |
| 50 mMol Citric acid/NaOH buffer pH 4.03 | 17.0% |

Description
Sterile base buffered RO1 saccharide solution
A5. Batch no NB01p44RO2
Non sterile

| Material | Weight fraction |
|---|---|
| Fructose | 52.0% |
| Glucose | 31.0% |
| 50 mMol Citric acid/NaOH buffer pH 4.03 | 17.0% |

Description
Non sterile base buffered RO2 saccharide solution.
A6. Batch no NB01p43RO2
Sterile

| Material | Weight fraction |
|---|---|
| Fructose | 52.0% |
| Glucose | 31.0% |
| 50 mMol Citric acid/NaOH buffer pH 4.03 | 17.0% |
| GOX enzyme | N/A |

Description Sterile base buffered RO2 saccharide solution
B. Unbuffered Samples
B1. Batch no NB01p51RO
Non sterile

| Material | Weight fraction |
|---|---|
| Fructose | 52.0% |
| Glucose | 31.0% |
| Water | 17.0% |

Description
Non sterile base buffered saccharide solution.
B2. Batch no NB01p51RO
Sterile

| Material | Weight fraction |
|---|---|
| Fructose | 52.0% |
| Glucose | 31.0% |
| Water | 17.0% |

Description Sterile base buffered saccharide solution
B3. Batch no NB01p51RO1
Non sterile

| Material | Weight fraction |
|---|---|
| Fructose | 52.0% |
| Glucose | 31.0% |
| Water | 17.0% |

Description
Non sterile base buffered RO1 saccharide solution.
B4. Batch no NB01p51RO1
Sterile

| Material | Weight fraction |
|---|---|
| Fructose | 52.0% |
| Glucose | 31.0% |
| Water | 17.0% |

Description
Sterile base buffered RO1 saccharide solution
B5. Batch no NB01p51RO2
Non sterile

| Material | Weight fraction |
|---|---|
| Fructose | 52.0% |
| Glucose | 31.0% |
| Water | 17 0% |

Description
Non sterile base buffered RO2 saccharide solution.
B6. Batch no NB01p51RO2
Sterile

| Material | Weight fraction |
|---|---|
| Fructose | 52.0% |
| Glucose | 31.0% |
| Water | 17.0% |

Description
Sterile base buffered RO2 saccharide solution
C. pH 7.04 Buffered Samples
C1. Batch no NB01p57RO
Non sterile

| Material | Weight fraction |
|---|---|
| Fructose | 52.0% |
| Glucose | 31.0% |
| 50 mMol Citric acid/NaOH buffer pH 7.04 | 17.0% |

Description
Non sterile base buffered saccharide solution.
C2. Batch no NB01p57RO
Sterile

| Material | Weight fraction |
|---|---|
| Fructose | 52.0% |
| Glucose | 31.0% |
| 50 mMol Citric acid/NaOH buffer pH 7.04 | 17.0% |

Description
Sterile base buffered saccharide solution
C3. Batch no NB01p57RO1
Non sterile

| Material | Weight fraction |
|---|---|
| Fructose | 52.0% |
| Glucose | 31.0% |
| 50 mMol Citric acid/NaOH buffer pH 7.04 | 17.0% |

Description
Non sterile base buffered RO1 saccharide solution.
C4. Batch no NB01p57RO1
Sterile

| Material | Weight fraction |
|---|---|
| Fructose | 52.0% |
| Glucose | 31.0% |
| 50 mMol Citric acid/NaOH buffer pH 7.04 | 17.0% |

Description
Sterile base buffered RO1 saccharide solution
C5. Batch no NB01p57RO2
Non sterile

| Material | Weight fraction |
|---|---|
| Fructose | 52.0% |
| Glucose | 31.0% |
| 50 mMol Citric acid/NaOH buffer pH 7.04 | 17.0% |

Description
Non sterile base buffered RO2 saccharide solution.
C6. Batch no NB01p57RO2

| Material | Weight fraction |
|---|---|
| Fructose | 52.0% |
| Glucose | 31.0% |
| 50 mMol Citric acid/NaOH buffer pH 7.04 | 17.0% |

Description
Sterile base buffered RO2 saccharide solution

Example 6—Efficacy of Synthetic Honey Compositions Against Planktonic MRSA

MIC and MBC were assessed for the RO1 samples (containing 50 ppm glucose oxidase) and compared to Surgihoney™ (also containing 50 ppm glucose oxidase).

See Andrews J. M. *Journal of Antimicrobial Chemotherapy* (2001) 48, suppl. S1, 5-16.

The results are shown in FIGS. 1 to 5.

The results show that, like Surgihoney, synthetic compositions containing glucose, glucose oxidase and fructose are able to inhibit microbial growth.

Out of all of synthetic compositions, the synthetic composition buffered at pH7.04 had the most effective MIC. Sterilised compositions were more effective than non-sterilised compositions, and synthetic composition buffered at pH7.04 synthetic had the most effective MBC when compared to other synthetic compositions and even when compared to SurgihoneyRO.

FIGS. 17 (*a* to *d*) and 18 show MIC and MBC results including SurgihoneyRO (RO2) samples and synthetic RO2 samples.

The invention claimed is:

1. A sterile composition comprising:
   an enzyme that is able to convert a substrate to release hydrogen peroxide;
   a substrate for the enzyme; and
   a superabsorbent component,
   wherein the composition is in the form of a powder, wherein the powder has a mean and/or modal particle diameter of 3000 μm or less, and wherein the composition does not contain any peroxidase.

2. A composition according to claim 1, wherein the superabsorbent component has an absorption capacity of at least 10 g/g.

3. A composition according to claim 1, wherein the absorption capacity is in respect of deionized water, distilled water, or a 0.9% (by weight) saline solution.

4. A composition according to claim 1, wherein the superabsorbent component is a superabsorbent polymer.

5. A composition according to claim 4, wherein:
   a) the superabsorbent polymer is anionic; and/or
   b) the superabsorbent polymer is cross-linked; and/or
   c) the superabsorbent polymer is polyacrylate or polyacrylamide.

6. A composition according to claim 4, wherein the superabsorbent polymer is selected from the group consisting of: a hydrolysed cellulose-polyacrylonitrile; a starch-polyacrylonitrile co-polymer; a cross-linked co-polymer of maleic anhydride; polyvinyl alcohol co-polymer; and cross-linked polyethylene oxide.

7. A composition according to claim 1, wherein the powder has a mean and/or modal particle diameter of 100 μm to 2000 μm.

8. A composition according to claim 1, wherein the enzyme is an oxidoreductase enzyme.

9. A composition according to claim 1, wherein the substrate is a sugar.

10. A composition according to claim 1, comprising a solute in the form of a sugar or sugar derivative having a solubility of at least 100 g/100 g water at 20° C. and 1 atm.

11. A composition according to claim 1, wherein the composition:
    a) Lacks catalase activity; and/or
    b) Comprises a blood clotting agent; and/or
    c) Does not contain zinc oxide; and/or
    d) Comprises a coagulation factor.

12. A composition according to claim 1, comprising a freeze-drying protective agent.

13. A wound dressing which comprises a dressing material and a composition according to claim 1.

14. An airtight container comprising a composition according to claim 1, the container comprising a one or a plurality of apertures for permitting dispensing of the composition, the one or plurality of apertures being sealed or covered prior to use.

15. A method for making a composition according to claim 1, comprising contacting a superabsorbent component with an enzyme that is able to convert a substrate to release hydrogen peroxide and a substrate for the enzyme.

16. A method of preventing, treating, or ameliorating a microbial infection, which comprises administering a composition according to claim 1, to a subject in need of such prevention, treatment or amelioration.

17. A method of treating a wound, which comprises administering a composition according to claim 1 to a wound site.

* * * * *